United States Patent [19]

Murphy et al.

[11] Patent Number: 5,654,155
[45] Date of Patent: Aug. 5, 1997

[54] CONSENSUS SEQUENCE OF THE HUMAN BRCA1 GENE

[75] Inventors: Patricia D. Murphy, Slingerland, N.Y.; Antonette C. Allen, Millersville, Md.; Christopher P. Alvares, Potomac, Md.; Brenda S. Critz, Frederick, Md.; Sheri J. Olson, Arlington, Va.; Denise B. Schelter, Burtonsville; Bin Zeng, Rockville, both of Md.

[73] Assignee: OncorMed, Inc., Gaithersburg, Md.

[21] Appl. No.: 598,591

[22] Filed: Feb. 12, 1996

[51] Int. Cl.$^6$ ............... C12Q 1/68; C12P 19/34; C07H 21/04; C07H 21/02
[52] U.S. Cl. ............ 435/6; 435/91.2; 536/23.1; 536/24.3; 536/24.33
[58] Field of Search .......... 435/6, 91.2; 536/23.1, 536/24.3, 24.33

[56] References Cited

U.S. PATENT DOCUMENTS 4,458,066 7/1984 Carothers et al. ............ 536/27

FOREIGN PATENT DOCUMENTS

0699754A1 3/1996 European Pat. Off. .
705903A 4/1996 European Pat. Off. .
0705903A1 4/1996 European Pat. Off. .
0705902A1 4/1996 European Pat. Off. .

OTHER PUBLICATIONS

Miki et al. Science 266: 66–71 1994.
Friedman et al. Nature Genetics 8: 399–404 Dec. 1994.
Scriver et al. In Variation in the Human Genome, Ciba Foundation Symposium 197, John Wiley & Sons eds, New York, pp. 73–96. 1996.
Roswell, S., et al., American Journal of Human Genetics 55:861–865, (1994).
Miki, Y., et al., Science 266:66–71, (1994).
Friend, S., et al., Nature Genetics 11:238, (1995).
Beaudet, Arthur L., et al.,: A Suggested Nomenclature for Designating Mutations. Human Mutation 2:245–248, 1993.
Friedman, Lori S., et al.,: Confirmation of BRCA1 by Analysis of Germline Mutations Linked to Breast and Ovarian Cancer. Nature Genetics 8: 399–404, Dec. 1994.
Shattuck–Eidens, Donna, et al.: A Collaborative Survey of 80 Mutations in the BRCA1 Breast and Ovarian Cancer Susceptibility Gene. JAMA 273:535–541, Feb. 15, 1995.
Ford, D., et al.,: The Genetics of Breast and Ovarian Cancer. Genetics Heterogeneity 5:805–811.

Szabo, Csilla I., et al., Inherited Breast and Ovarian Cancer. Human Molecular Genetics 4:1811–1817, 1995.
Plummer, S.J., et al., Detection of BRAC1 Mutations by the Protein Truncation Test 4:1989–1991, 1995.
Chen, Y., et al., Aberrant Subcellular Localization of BRCA1 in Breast Cancer. Science 270: 789–791, Nov. 3, 1995.
Gayther, Simon A., et al., Germline Mutations of the BRCA1 Gene in Breast and Ovarian Cancer Families Provide Evidence for A Genotype–phenotype Correlation. Nature Genetics 11: 428–433, Dec. 1995.
Durocher, F., et al., Comparison of BRCA1 Polymorphisms, Rare Sequence Variants and/or Missense Mutations in Unaffected and Breast/Ovarian Cancer Populations 5: 835–842, 1996.
Berman, D.B., et al., Two District Origins of a Common BRCA1 Mutation in Breast–Ovarian Cancer Families: A Genetic Study of 15 185delAG–Mutation Kindreds. Am. J. Hum. Genet. 58:1166–1176, 1996.
Schultz, D.C., et al., Identification of Two Candidate Tumor Suppressor Genes on Chromosome 17p13.3$^1$. Cancer Research 56:1997–2002, May 1, 1996.
Couch, Fergus J., et al., Mutations and Polymorphisms in the Familial Early–Onset Breast Cancer (BRCA1) Gene. Human Mutation 8:8–18, 1996.
Sanger, F., et al., J. Mol. Biol. 42:1617, (1980).
Beaucage, et al., Tetrahedron Letter. 22:1859–1862.
Maniatis, et al., In Molecular Cloning: A Laboratory Manual, Cold Spring, NY, pp. 280–281, (1982).
Conner, et al., Proc. Natl. Acad. Sci. U.S.A. 80:278, (1983).
Saiki, et al., Bio/Technology 3: 1088–1012 (1985).
Landegren, et al., Science 241:1007, (1988).
Landgren, et al., Science 242:229–237, (1988).
McPherson, M.J., et al., PCR. A Practical Approach. ILR Press, Eds. (1992).
Easton, et al., American Journal of Human Genetics 52: 678–701, (1993).

*Primary Examiner*—W. Gary Jones
*Assistant Examiner*—Dianne Rees
*Attorney, Agent, or Firm*—R. Thomas Gallegos; Albert P. Halluin

[57] ABSTRACT

A consensus DNA sequence has been determined for the BRCA1 gene. As has been seven polymorphic sites and their rates of occurrence in normal BRCA1 genes. The consensus gene BRCA1$^{(omi)}$ and the seven polymorphic sites will provide greater accuracy and reliability for genetic testing. One skilled in the art will be better able to avoid misinterpretations of changes in the gene, determine the presence of a normal gene, and of mutations, and to classify tumors.

4 Claims, No Drawings

CONSENSUS SEQUENCE OF THE HUMAN BRCA1 GENE

FIELD OF THE INVENTION

This invention relates to a gene which has been associated with breast and ovarian cancer where the gene is found to be mutated. More specifically, this invention relates to the most likely sequence (i.e. "Consensus Normal DNA sequence") for the BRCA1 gene (BRCA1$^{(omi)}$ SEQ. ID. NO: 1) in normal individuals.

BACKGROUND OF THE INVENTION

It has been estimated that about 5–10% of breast cancer is inherited Rowell, S., et al., *American Journal of Human Genetics* 55:861–865 (1994). Located on chromosome 17, BRCA1 is the first gene identified to be conferring increased risk for breast and ovarian cancer. Miki et al., *Science* 266:66–71 (1994). Mutations in this "tumor suppressor" gene are thought to account for roughly 45% of inherited breast cancer and 80–90% of families with increased risk of early onset breast and ovarian cancer. Easton et al., *American Journal of Human Genetics* 52:678–701 (1993).

Locating one or more mutations in the BRCA1 region of chromosome 17 provides a promising approach to reducing the high incidence and mortality associated with breast and ovarian cancer through the early detection of women at high risk. These women, once identified, can be targeted for more aggressive prevention programs. Screening is carried out by a variety of methods which include karyotyping, probe binding and DNA sequencing.

In DNA sequencing technology, genomic DNA is extracted from whole blood and the coding regions of the BRCA1 gene are amplified. Each of the coding regions is sequenced completely and the results are compared to the normal DNA sequence of the gene.

The BRCA1 gene is divided into 24 separate exons. Exons 1 and 4 are noncoding, in that they are not part of the final functional BRCA1 protein product. The BRCA1 coding region spans roughly 5600 base pairs (bp). Each exon consists of 200–400 bp, except for exon 11 which contains about 3600 bp. To sequence the coding region of the BRCA1 gene, each exon is amplified separately and the resulting PCR products are sequenced in the forward and reverse directions. Because exon 11 is so large, we have divided it into twelve overlapping PCR fragments of roughly 350 bp each (segments "A" through "L" of BRCA1 exon 11).

Many mutations and normal polymorphisms have already been reported in the BRCA1 gene. A world wide web site has been built to facilitate the detection and characterization of alterations in breast cancer susceptibility genes. Such mutations in BRCA1 can be accessed through the Breast Cancer Information Core at: http://www.nchgr.nih.gov/dir/lab_transfer/bic. This data site became publicly available on Nov. 1, 1995. Friend, S. et al. *Nature Genetics* 11:238, (1995).

The genetics of Breast/Ovarian Cancer Syndrome is autosomal dominant with reduced penetrance. In simple terms, this means that the syndrome runs through families such that both sexes can be carriers (only women get the disease but men can pass it on), all generations will likely have breast/ovarian or both diseases and sometimes in the same individual, occasionally women carriers either die young before they have the time to manifest disease (and yet offspring get it) or they never develop breast or ovarian cancer and die of old age (the latter people are said to have "reduced penetrance" because they never develop cancer). Pedigree analysis and genetic counseling is absolutely essential to the proper workup of a family prior to any lab work.

Until now, only a single normal sequence for BRCA1 has been available for comparison. That sequence is available as GenBank Accession Number U15595. There is a need in the art, therefore, to have available a normal sequence which represents most likely BRCA1 sequence to be found in the majority of the normal population, the (i.e. "Consensus Normal DNA sequence"). A Consensus Normal DNA sequence will make it possible for true mutations to be easily identified or differentiated from polymorphisms. Identification of mutations of the BRCA1 gene and protein would allow more widespread diagnostic screening for hereditary breast and ovarian cancer than is currently possible.

A consensus normal gene sequence of the BRCA1 is provided which more accurately reflects the most likely sequence to be found in a subject. Use of the consensus normal gene sequence (BRCA1$^{(omi)}$SEQ ID. NO: 1), rather than the previously published BRCA1 sequence, will reduce the likelihood of misinterpreting a "sequence variation" found in the normal population with a pathologic "mutation" (i.e. causes disease in the individual or puts the individual at a high risk of developing the disease). With large interest in breast cancer predisposition testing, misinterpretation is particularly worrisome. People who already have breast cancer are asking the clinical question: "is my disease caused by a heritable genetic mutation?" The relatives of the those with breast cancer are asking the question: "Am I also a carrier of the mutation my relative has? Thus, is my risk increased, and should I undergo a more aggressive surveillance program."

SUMMARY OF THE INVENTION

The present invention is based on the discovery of the most likely sequence to be found in normal human individuals for the BRCA1 gene.

It is an object of the invention to provide a consensus sequence for the normal BRCA1 gene, i.e. the consensus Sequence having the more commonly occurring nucleotides where normal polymorphisms occur.

It is another object of the invention to provide a consensus normal protein sequence of the BRCA1 protein It is another object of the invention to provide a list of the codon pairs which occur at each of seven polymorphic points on the normal BRCA1 gene.

It is another object of the invention to provide the rates of occurrence for the codons.

It is another object of the invention to provide a method wherein BRCA1, or parts thereof, is amplified with one or more oligonucleotide primers.

It is another object of this invention to provide a method of avoiding misinterpretation of changes which a laboratory may find in the BRCA1 gene.

It is another object of this invention to provide a method of identifying individuals who carry no mutation(s) of the BRCA1 gene and are therefore at no increased risk or susceptibility to breast or ovarian cancer based on a finding that the individual does not carry an abnormal BRCA1 gene.

It is another object of this invention to provide a method of identifying a mutation leading to predisposition or higher susceptibility to breast or ovarian cancer.

It is another object of the invention to provide a method of classifying a tumor for diagnostic and prognostic purposes.

There is a need in the art for a consensus normal sequence of the BRCA1 gene and for the consensus normal protein sequence of BRCA1 as well as for an accurate list of codons which occur at polymorphic points on a normal sequence. A person skilled in the art of genetic susceptibility testing will find the present invention useful for:

a) identifying individuals having a normal BRCA1 gene, who are therefore not at risk or have no increased susceptibility to breast or ovarian cancer from a BRCA1 mutation;

b) avoiding misinterpretation of normal polymorphisms found in the normal BRCA1 gene;

c) determining the presence of a previously unknown mutation in the BRCA1 gene.

d) identifying a mutation which indicates a predisposition or higher susceptibility to breast or ovarian cancer; or for e) classifying a tumor for diagnostic and prognostic purposes.

f) performing gene repair.

DETAILED DESCRIPTION OF THE INVENTION

Definitions

The following definitions are provided for the purpose of understanding this invention.

"Consensus Normal Sequence" refers to the nucleic acid or protein sequence, the nucleic or amino acids of which are known to occur with high frequency in a population of individuals who carry the gene which codes for a normally functioning protein, or which nucleic acid itself has normal function.

"Consensus normal DNA sequence" also called "consensus normal gene sequence" refers to a nucleic acid sequence, the nucleic acid of which are known to occur at their respective positions with high frequency in a population of individuals who carry the gene which codes for a normally functioning protein, or which itself has normal function.

"Consensus Normal Protein Sequence" refers to the protein sequence, the amino acids of which are known to occur with high frequency in a population of individuals who carry the gene which codes for a normally functioning protein. "BRCA1$^{(omi)}$(SEQ ID NO: 1)" refers to a consensus sequence for the BRCA1 gene. The consensus sequence was found by end to end sequencing,of the BRCA1 gene from 5 individuals randomly drawn from the population and found to have no family history of breast or ovarian cancer. The sequenced gene was found not to contain any mutations. The consensus was determined by calculating the frequency with which nucleic acids occur and inserting the nucleic acid with highest frequency of occurrence at each polymorphic site. In some cases the insertion of a nucleic acid at a polymorphic site indicated a codon change and a change of amino acid from previously published information. In other cases the frequency of occurrence of a nucleic acid was found to differ from the published frequency.

The term "primer" as used herein refers to a sequence comprising about 20 or more nucleotides of the BRCA1 gene.

A "target polynucleotide" refers to the nucleic acid sequence of interest e.g., the BRCA1 encoding polynucleotide. Other primers which can be used for primer hybridization will be known or readily ascertainable to those of skill in the art.

The term "substantially complementary to" or "substantially the sequence" refers to primer sequences which hybridize to the sequences provided under stringent conditions and/or sequences having sufficient homology with BRCA1 sequences, such that the allele specific oligonucleotide primers hybridize to the BRCA1 sequences to which they are complimentary.

The term "isolated" as used herein includes oligonucleotides substantially free of other nucleic acids, proteins, lipids, carbohydrates or other materials with which they may be associated. Such association is typically either in cellular material or in a synthesis medium.

Sequencing

Any nucleic acid specimen, in purified or non-purified form, can be utilized as the starting nucleic acid or acids, providing it contains, or is suspected of containing, the specific nucleic acid sequence containing a polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. See TABLE II. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al. in *Molecular Cloning:A Laboratory Manual*, Cold Spring Harbor, N.Y., p 280–281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The allele specific oligonucleotide primers are useful in determining whether a subject is at risk of having breast or ovarian cancer, and also useful for characterizing a tumor. Primers direct amplification of a target polynucleotide prior to sequencing. These unique BRCA1 oligonucleotide primers of TABLE II were designed and produced specifically to optimize amplification of portions of BRCA1 which are to be sequenced.

The primers used to carry out this invention embrace oligonucleotides of sufficient length and appropriate sequence to provide initiation of polyrmerization. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers used to carry out this invention are designed to be substantially complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859–1862, 1981. One method for synthesizing oligonucleotides on a modified solid support is described in U.S. Pat. No. 4,458,066.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase, polymerase muteins, reverse transcriptase, other enzymes, including heat-stable enzymes (e.i., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion.

Amplification is described in *PCR. A Practical Approach*, ILR Press, Eds. M. J. McPherson, P. Quirke, and G. R. Taylor, 1992.

The amplification products may be detected by Southern blots analysis, without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., *Bio/Technology*,3:1008–1012, 1985), allele-specific oligonucleotide (ASO) probe analysis (Conner, et. al., *Proc. Natl. Acad. Sci.* U.S.A., 80:278, 1983), oligonucleotide ligation assays (OLAs) (Landgren, et. al., *Science*,241:1007, 1988), and the like. Molecular techniques for DNA analysis have been reviewed (Landgren, et. al., *Science*, 242:229–237, 1988).

Preferably, the method of amplifying is by PCR, as described herein and as is commonly used by those of ordinary skill in the art. Alternative methods of amplification have been described and can also be employed as long as the BRCA1 locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for hincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling. Another amplification system useful in the method of the invention is the QB Replicase System. Although PCR is the preferred method of amplification if the invention, these other methods can also be used to amplify the BRCA1 locus as described in the method of the invention.

The BRCA1$^{(omi)}$ Consensus Normal DNA sequence was obtained by end to end sequencing of five normal subjects in the manner described above followed by analysis of the data obtained. The data obtained provided us with the opportunity to evaluate six previously published normal polymorphisms for correctness and frequency in the population, and to identify an additional polymorphism not previously found.

The consensus normal gene sequence can be used for gene therapy. A complete description of the method is provided in Anderson et al. U.S. Pat. No. 5,399,346, issued Mar. 21, 1995. The isolated consensus normal BRCA1 gene can be constructed from amplification products and inserted into a vector such as the LXSN vector. Fresh lymphocytes of a patient having a mutation in the BRCA1 gene, are cultured. The cells are transduced with the vector above, and culturing is continued. The cultured, transformed cells are infused into the patient.

The consensus normal BRCA1 amino acid sequence may be used to make diagnostic probes. Labeled diagnostic probes may be used by any hybridization method to determine the level of BRCA1 protein in serum or lysed cell suspension of a patient, or solid surface cell sample.

The consensus normal BRCA1 amino acid sequence may be used to provide a level of protection for patients against risk of breast or ovarian cancer. The isolated consensus normal BRCA1 gene can be constructed from amplification products and inserted into a vector such as the LXSN vector. Fresh lymphocytes of a patient having a mutation in the BRCA1 gene, are cultured. The cells are transduced with the vector above, and cultured. Extracted BRCA1 protein can be provided by injection or other known means to patients who are at risk.

EXAMPLE 1

Determination of the Sequence of the BRCA1$^{(omi)}$ Gene From Five Normal Individuals Materials and Methods Approximately 150 volunteers were screened in order to identify individuals with no cancer history in their immediate family (i.e. first and second degree relatives). Each person was asked to fill out a hereditary cancer prescreening questionnaire See TABLE I below. Five of these were randomly chosen for end-to-end sequencing of their BRCA1 gene." A first degree relative is a parent, sibling, or off spring. A second degree relative is an aunt, uncle, grandparent, grandchild, niece, nephew, or half-sibling.

TABLE I

Hereditary Cancer Pre-Screening Questionnaire

Part A: Answer the following questions about your family

1. To your knowledge, has anyone in your family been diagnosed with a very specific hereditary colon disease called Familial Adenomatous Polyposis (FAP)?
2. To your knowledge, have you or any aunt had breast cancer diagnosed before the age 35?
3. Have you had Inflammatory Bowel Disease, also called Crohn's Disease or Ulcerative Colitis, for more than 7 years?

Part B: Refer to the list of cancers below for your responses only to questions in Part B

| Bladder Cancer | Lung Cancer | Pancreatic Cancer |
| Breast Cancer | Gastric Cancer | Prostate Cancer |
| Colon Cancer | Malignant Melanoma | Renal Cancer |
| Endometrial Cancer | Ovarian Cancer | Thyroid Cancer |

4. Have your mother or father, your sisters or brothers or your children had any of the listed cancers?
5. Have there been diagnosed in your mother's brothers or sisters, or your mother's parents more than one of the cancers in the above list?
6. Have there been diagnosed in your father's brothers or sisters, or your father's parents more than one of the cancers in the above list?

Part C: Refer to the list of relatives below for responses only to questions in Part C

| You | Your mother |
| Your sisters or brothers | Your mothers's sisters or brothers (maternal aunts and uncles) |
| Your children | Your mother's parents (maternal grandparents) |

7 Have there been diagnosed in these relatives 2 or more identical types of cancer?
   Do not count "simple" skin cancer, also called basal cell or squamous cell skin cancer.
8. Is there a total of 4 or more of any cancers in the list of relatives above other than "simple" skin cancers?

Part D: Refer to the list of relatives below for responses only to questions in Part D.

| You | Your father |
| Your sisters or brothers | Your fathers's sisters or brothers (paternal aunts and uncles) |
| Your children | Your father's parents (paternal grandparents) |

TABLE I-continued

Hereditary Cancer Pre-Screening Questionnaire

9. Have there been diagnosed in these relatives 2 or more identical types of cancer?
   Do not count "simple" skin cancer, also called basal cell or squamous cell skin cancer.
10. Is there a total of 4 or more of any cancers in the list of relatives above other than "simple" skin cancers?

© Copyright 1996, OncorMed, Inc.

Genomic DNA was isolated from white blood cells of five normal subjects selected from analysis of their answers to the questions above. Dideoxy sequence analysis was performed following polymerase chain reaction amplification.

All exons of the BRCA1 gene were subjected to direct dideoxy sequence analysis by asymmetric amplification using the polymerase chain reaction (PCR) to generate a single stranded product amplified from this DNA sample. Shuldiner, et at., Handbook of Techniques in Endocrine Research, p. 457–486, DePablo, F., Scanes, C., eds., Academic Press, Inc., 1993. Fluorescent dye was attached for automated sequencing using the Taq Dye Terminator Kit (PERKIN-ELMER® cat# 401628). DNA sequencing was performed in both forward and reverse directions on an Applied Biosystems, Inc. (ABI) automated sequencer (Model 377). The software used for analysis of the resulting data was "Sequence Navigator" purchased through ABI.

1. Polymerase Chain Reaction (PCR) Amplification

Genomic DNA (100 nanograms) extracted from white blood cells of five normal subjects. Each of the five samples was sequenced end to end. Each sample was amplified in a final volume of 25 microliters containing 1 microliter (100 nanograms) genomic DNA, 2.5 microliters 10X PCR buffer (100 mM Tris, pH 8.3, 500 mM KCl, 1.2 mM $MgCl_2$), 2.5 microliters 10X dNTP mix (2 mM each nucleotide), 2.5 microliters forward primer, 2.5 microliters reverse primer, and 1 microliter Taq polymerase (5 units), and 13 microliters of water.

The primers in Table II, below were used to carry out amplification of the various sections of the BRCA1 gene samples. The primers were synthesized on an DNA/RNA Synthesizer Model 394®.

TABLE II

BRCA1 PRIMERS AND SEQUENCING DATA

| EXON | | SEQUENCE | SEQ. ID NO. | MER | $MG^2+1$ | SIZE |
|---|---|---|---|---|---|---|
| EXON 2 | 2F | 5' GAA GTT GTC ATT TTA TAA ACC TTT-3' | 3 | 24 | 1.6 | ~275 |
|  | 2R | 5' TFT CTT TTC TTC CCT AGT ATG 5-3' | 4 | 22 |  |  |
| EXON 3 | 3F | 5' TCC TGA CAC AGC AGA CAT TTA-3' | 5 | 21 | 1.4 | ~375 |
|  | 3R | 5' TTG GAT TTT CGT TCT CAC TTA-3' | 6 | 21 |  |  |
| EXON 5 | 5F | 5' CTC TTA AGG GCA GTT GTG AG-3' | 7 | 20 | 1.2 | ~275 |
|  | ¹5R | 5' TTC CTA CTG TGG TTG CTT CC | 8 | 20* |  |  |
| EXON 6 | 6/7F | 5' CTT ATT TTA GTG TCC TTA AAA GG-3' | 9 | 23 | 1.6 | ~250 |
|  | 6R | 5' TTT CAT GGA CAG CAC TTG AGT G-3' | 10 | 22 |  |  |
| EXON 7 | 7F | 5' CAC AAC AA GAG CAT ACA TAG GG-3' | 11 | 23 | 1.5 | ~275 |
|  | 6/7R | 5' TCG GGT TCA CTC TGT AGA AG-3' | 12 | 20 |  |  |
| EXON 8 | 8F1 | 5' TTC TCT TCA GGA GGA AAA GCA-3' | 13 | 21 | 1.2 | ~270 |
|  | 8R1 | 5' GCT GCC TAC CAC AAA TAC AAA-3' | 14 | 21 |  |  |
| EXON 9 | 9F | 5' CCA CAG TAG ATG CTC AGT AAATA-3' | 15 | 23 | 1.2 | ~250 |
|  | 9R | 5' TAG GAA AAT ACC AGC TTC ATA GA-3' | 16 | 23 |  |  |
| EXOM 10 | 10F | 5' TGG TCA GCT TTC TGT AAT CG-3' | 17 | 20 | 1.6 | ~250 |
|  | 10R | 5' GTA TCT ACC CAC TCT CTT CTT CAG-3' | 18 | 24 |  |  |
| EXON 11A | 11AF | 5' CCA CCT CCA AGG TGT ATC A-3' | 19 | 19 | 1.2 | 372 |
|  | 11AR | 5' TGT TAT GTT GGC TCC TTG CT-3' | 20 | 20 |  |  |
| EXON 11B | 11BF1 | 5' CAC TAA AGA CAG AAT GAA TCT A-3; | 21 | 21 | 1.2 | ~400 |
|  | 11BR1 | 5' GAA GAA CCA GAA TAT TCA TCT A-3' | 22 | 21 |  |  |
| EXON 11C | 11CF1 | 5' TGA TGG GGA GTC TGA ATC AA-3' | 23 | 20 | 1.2 | ~400 |
|  | 11CR1 | 5' TCT GCT TTC TTG ATA AAA TCC T-3' | 24 | 22 |  |  |
| EXON 11D | 11DF1 | 5' AGC GTC CCC TCA CAA ATA AA-3' | 25 | 20 | 1.2 | ~400 |
|  | 11DR1 | 5' TCA AGC GCA TGA ATA TGC CT-3' | 26 | 20 |  |  |
| EXON 11E | 11EF | 5' GTA TAA GCA ATA TGG AAC TCG A-3' | 27 | 22 | 1.2 | 388 |
|  | 11ER | 5' TTA AGT TCA CTG GTA TTT GAA CA-3' | 28 | 23 |  |  |
| EXON 11F | 11FF | 5' GAC AGC GAT ACT TTC CCA GA-3' | 29 | 20 | 1.2 | 382 |
|  | 11FR | 5' TGG AAC AAC CAT GAA TTA GTC-3' | 30 | 21 |  |  |
| EXON 11G | 11GF | 5' GGA AGT TAG CAC TCT AGG GA-3' | 31 | 20 | 1.2 | 423 |
|  | 11GR | 5' GCA GTG ATA TTA ACT GTC TGT A-3' | 32 | 22 |  |  |
| EXON 11H | 11HF | 5' TGG GTC CTT AAAGAA ACA AAGT-3' | 33 | 22 | 1.2 | 366 |
|  | 11HR | 5' TCA GGT GAC ATT GAA TCT TCC-3' | 34 | 21 |  |  |
| EXON 11I | 11IF | 5' CCA CTT TTT CCC ATC AAG TCA-3' | 35 | 21 | 1.2 | 377 |
|  | 11IR | 5' TCA GGA TGC TTA CAA TTA CTT C-3' | 36 | 21 |  |  |
| EXON 11J | 11JF | 5' CAA AAT TGA ATG CTA TGC TAA GA-3' | 37 | 23 | 1.2 | 377 |
|  | 11JR | 5' TCG GTA ACC CTG AGC CAA AT-3' | 38 | 20 |  |  |
| EXON 11K | 11KF | 5' GCA AAAGCG TCC AGA AAG GA-3' | 39 | 20 | 1.2 | 396 |
|  | 11KR-1 | 5' TAT TTG CAG TCA AGT CTT CCA A-3' | 40 | 22 |  |  |
| EXON 11L | 11LF-1 | 5' GTA ATA TTG GCA AAG GCA TCT-3' | 41 | 22 | 1.2 | 360 |
|  | 11LR | 5' TAA AAT GTG CTC CCC AAA AGC A-3' | 42 | 22 |  |  |
| EXON 12 | 12F | 5' GTC CTG CCA ATG AGA AGA AA-3' | 43 | 20 | 1.2 | ~300 |
|  | 12R | 5' TGT CAG CAA ACC TAA GAA TGT-3' | 44 | 21 |  |  |
| EXON 13 | 13F | 5' AAT GGA AAG CTT CTC AAAGTA-3' | 45 | 21 | 1.2 | ~325 |
|  | 13R | 5' ATG TTG GAG CTA GGT CCT TAC-3' | 46 | 21 |  |  |
| EXON 14 | 14F | 5' CTA ACC TGA ATT ATC ACT ATC A-3' | 47 | 22 | 1.2 | ~310 |
|  | 14R | 5' GTG TAT AAATGC CTG TAT GCA-3' | 48 | 21 |  |  |

TABLE II-continued

BRCA1 PRIMERS AND SEQUENCING DATA

| EXON | SEQUENCE | | SEQ. ID NO. | MER | MG² + 1 | SIZE |
|---|---|---|---|---|---|---|
| EXON 15 | 15F | 5' TGG CTG CCC AGG AAG TAT G-3' | 49 | 19 | 1.2 | ~375 |
| | 15R | 5' AAC CAG AAT ATC TTT ATG TAG GA-3' | 50 | 23 | | |
| EXON 16 | 16F | 5' AAT TCT TAA CAG AGA CCA GAA C-3' | 51 | 22 | 1.6 | ~550 |
| | 16R | 5' AAA ACT CTT TCC AGA ATG TTG 5-3' | 52 | 22 | | |
| EXON 17 | 17F | 5' GTG TAG AAC GTG CAG GAT TG-3' | 53 | 20 | 1.2 | ~275 |
| | 17R | 5' TCG CCT CAT GTG GTT TTA-3' | 54 | 18 | | |
| EXON 18 | 18F | 5' GGC TCT TTA GCT TCT TAG GAC-3' | 55 | 21 | 1.2 | ~350 |
| | 18R | 5' GAG ACC ATT TTC CCA GCA TC-3' | 56 | 20 | | |
| EXON 19 | 19F | 5' CTG TCA TTC TTC CTG TGC TC-3' | 57 | 20 | 1.2 | ~250 |
| | 19R | 5' CAT TGT TAA GGA AAG TGG TGC-3' | 58 | 21 | | |
| EXON 20 | 20F | 5' ATA TGA CGT GTC TGC TCC AC-3' | 59 | 20 | 1.2 | ~425 |
| | 20R | 5' GGG AAT CCA AAT TAC ACA GC-3' | 60 | 20 | | |
| EXON 21 | 21F | 5' AAG CTC TTC CTT TTT GAA AGT C-3' | 61 | 22 | 1.6 | ~300 |
| | 21R | 5' GTA GAG AAA TAG AAT AGC CTC T-3' | 62 | 22 | | |
| EXON 22 | 22F | 5' TCC CAT TGA GAG GTC TTG CT-3' | 63 | 20 | 1.6 | ~300 |
| | 22R | 5' GAG AAG ACT TCT GAG GCT AC-3' | 64 | 20 | | |
| EXON 23 | 23F-1 | 5' TGA AGT GAC AGT TCC AGT AGT-3' | 65 | 21 | 1.2 | ~250 |
| | 23R-1 | 5' CAT TTT AGC CAT TCA TTC AAC AA-3' | 66 | 23 | | |
| EXON 24 | 24F | 5' ATG AAT TGA CAC TAA TCT CTG C-3' | 67 | 22 | 1.4 | ~285 |
| | 24R | 5' GTA GCC AGG ACA GTA GAA GGA-3' | 68 | 2.1 | | |

Thirty-five cycles were performed, each consisting of denaturing (95° C.; 30 seconds), annealing (55° C.; 1 minute), and extension (72° C.; 90 seconds), except during the first cycle in which the denaturing time was increased to 5 minutes, and during the last cycle in which the extension time was increased to 5 minutes.

PCR products were purified using QIA-QUICK® PCR purification kits (QIAGEN, cat# 28104; Chatsworth, Calif.). Yield and purity of the PCR product determined spectrophotometrically at $OD_{260}$ on a Beckman DU 650 spectrophotometer.

2. Dideoxy Sequence Analysis

Fluorescent dye was attached to PCR products for automated sequencing using the Taq Dye Terminator Kit (PERKIN-ELMER® cat#401628). DNA sequencing was performed in both forward and reverse directions on an Applied Biosystems, Inc. (ABI) Foster City, Calif., automated sequencer (Model 377). The software used for analysis of the resulting data was "SEQUENCE NAVIGATOR®" purchased through ABI.

3. Results

Differences in the nucleic acids of the five normal individuals were found in seven locations on the gene. The changes and their positions are found on TABLE III, below.

TABLE III

NORMAL PANEL TYPING

| AMINO ACID CHANGE | EXON | 1 | 2 | 3 | 4 | 5 | FREQUENCY |
|---|---|---|---|---|---|---|---|
| SER(SER) (694) | 11E | C/C | C/T | C/T | T/T | T/T | 0.4 C 0.6 T |
| LEU(LEU) (771) | 11F | T/T | C/T | C/T | C/C | C/C | 0.4 T 0.6 C |
| PRO(LEU) (871) | 11G | C/T | C/T | C/T | T/T | T/T | 0.3 C 0.7 T |
| GLU(GLY) (1038) | 11I | A/A | A/G | A/G | G/G | G/G | 0.4 A 0.6 G |
| LYS(ARG) (1183) | 11J | A/A | A/G | A/G | G/G | G/G | 0.4 A 0.6 G |
| SER(SER) (1436) | 13 | T/T | T/T | T/C | C/C | C/C | 0.5 T 0.5 T |
| SER(GLY) (1613) | 16 | A/A | A/G | A/G | G/G | G/G | 0.4 A 0.6 G |

A consensus normal sequence of the BRCA1 gene was determined by calculating the percentage of occurrence of each polymorphism and inserting the more frequently occurring polymorphism into the published BRCA1 (Genbank Accession Number U15595). The normal consensus BRCA1$^{(omi)}$ is shown as SEQ. ID NO. 1 at page 29.

The data show that for each of the samples. The BRCA1 gene is identical except in the region of seven polymorphisms. These polymorphic regions, together with their locations, the amino acid groups of each codon, the frequency of their occurence and the amino acid coded for by each codon are found in TABLE IV below.

TABLE IV

CODON AND BASE CHANGES IN SEVEN POLYMORPHIC SITES OF BRCA1 NORMAL GENE

| SAMPLE NUMBER | BASE CHANGE | POSITION | EXON | CODON CHANGE | AA CHANGE | PUBLISHED FREQUENCY | [2]REFERENCES |
|---|---|---|---|---|---|---|---|
| 2, 3, 4, 5 | C-T | 2201 | 11E | AGC(AGT) | SER—SER (694) | C | UNPUBLISHED |
| 2, 3, 4, 5 | T-C | 2430 | 11F | TTG(CTG) | LEU—LEU (771) | T = 67% | 13 |
| 1, 2, 3, 4, 5 | C-T | 2731 | 11G | CCG(CTG) | PRO—LEU (871) | T = 66% | 12 |
| 2, 3, 4, 5 | A-G | 3232 | 11I | GAA(GGA) | GLU—GLY (1038) | A = 67% | 13 |
| 2, 3, 4, 5 | A-G | 3667 | 11J | AAA(AGA) | LYS—ARG (1183) | A = 68% | 12 |
| 3, 4, 5 | T-C | 4427 | 13 | TCT(TCC) | SER—SER (1436) | T = 67% | 12 |
| 2, 3, 4, 5 | A-G | 4956 | 16 | AGT(GGT) | SER—GLY (1613) | A = 67% | 12 |

[2]Reference numbers correspond To The Table Of References on Page 28.

EXAMPLE 2

Determination of a Normal Individual Using BRCA1$^{(omi)}$ and the Seven Polymorphisms for Reference A person skilled in the art of genetic susceptibility testing will find the present invention useful for:

a) identifying individuals having a normal BRCA1 gene, who are therefore not at risk or have no increased susceptibility to breast or ovarian cancer from a BRCA1 mutation;

b) avoiding misinterpretation of normal polymorphisms found in the normal BRCA1 gene;

Sequencing is carried out as in EXAMPLE 1 using a blood sample from the patient in question. However, the BRCA1$^{(omi)}$ sequence is used for reference and polymorphic sites are compared to the nucleic acid sequences listed above for normal codons at each polymophic site. A normal sample is one which compares to the BRCA1$^{(omi)}$ sequence and contains one of the normal base variations which occur at each of the polymorphic sites. The codons which occur at each of the polymorphic sites are paired below.

AGC and AGT at position 2201,

TTG and CTG at position 2430,

CCG and CTG at position 2731,

GAA and GGA at position 3232,

AAA and AGA at position 3667,

TCT and TCC at position 4427, and

AGT and GGT at position 4956.

The availability of these polymorphic pairs provides added assurance that one skilled in the art can correctly interpret the polymorphic variations without mistaking a normal variation for a mutation.

Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the Taq Dye Terminator Kit (PERKIN-ELMER® cat# 401628). DNA sequencing is performed in both forward and reverse directions on an Applied Biosystems, Inc. (ABI) automated Sequencer (Model 377). The software used for analysis of the resulting data is "SEQUENCE NAVIGATOR®" purchased through ABI.

1. Polymer Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10X PCR buffer (100 mM Tris, pH 8.3, 500 mM KCl, 1.2 mM MgCl$_2$), 2.5 microliters 10X dNTP mix (2 mM each nucleotide), 2.5 microliters forward primer (BRCA1-11K-F, 10 micromolar solution), 2.5 microliters reverse primer (BRCA1-11K-R, 10 micromolar solution),and 1 microliter Taq polymerase (5 units), and 13 microliters of water. The PCR primers used to amplify a patient's sample BRCA1 gene are listed in Table II. The primers were synthesized on an DNA/RNA Synthesizer Model 394®. Thirty-five cycles are of amplification are performed, each consisting of denaturing (95° C.; 30 seconds), annealing (55° C.; 1 minute), and extension (72° C.; 90 seconds), except during the first cycle in which the denaturing time is increased to 5 minutes, and during the last cycle in which the extension time is increased to 5 minutes.

PCR products are purified using QIA-QUICK® PCR purification kits (QIAGEN®, cat# 28104; Chatsworth, Calif.). Yield and purity of the PCR product determined spectrophotometrically at OD$_{260}$ on a Beckman DU 650 spectrophotometer.

2. Dideoxy Sequence Analysis

Fluorescent dye is attached to PCR products for automated sequencing using the Taq Dye Terminator Kit (PERKIN-ELMER® cat# 401628). DNA sequencing is performed in both forward and reverse directions on an Applied Biosystems, Inc. (ABI) Foster City, Calif., automated sequencer (Model 377). The software used for analysis of the resulting data is "SEQUENCE NAVIGATOR®" purchased through ABI. The BRCA1$^{(omi)}$ sequence is entered into the Sequence Navigator software as the Standard for comparison. The Sequence Navigator software compares the sample sequence to the BRCA1$^{(omi)}$ standard, base by base. The Sequence Navigator highlights all differences between the BRCA1$^{(omi)}$ (SEQ ID. NO: 1) consensus normal DNA sequence and the patient's sample sequence.

A first technologist checks the computerized results by comparing visually the BRCA1$^{(omi)}$ standard against the patient's sample, and again highlights any differences between the standard and the sample. The first primary technologist then interprets the sequence variations at each position along the sequence. Chromatograms from each sequence variation are generated by the Sequence Navigator and printed on a color printer. The peaks are interpreted by the first primary technologist and a second primary technologist. A secondary technologist then reviews the chromatograms. The results are finally interpreted by a geneticist. In each instance, a variation is compared to known normal polymorphisms for position and base change. If the sample BRCA1 sequence matches the BRCA1$^{(omi)}$ standard, with only variations within the known list of polymorphisms, it is interpreted as a normal gene sequence.

EXAMPLE 3

Determining the Presence of a Mutation in the BRCA1 Gene Using BRCA1$^{(omi)}$ and Seven Polymorphisms for Reference A person skilled in the art of genetic susceptibility testing will find the present invention useful for determining the presence of a known or previously unknown mutation in the BRCA1 gene. A list of mutations of BRCA1 is publicly available in the Breast Cancer Information Core at: http://www.nchgr.nih.gov/dir/lab_transfer/bic. This data site became publicly available on Nov. 1, 1995. Friend, S. et al. *Nature Genetics* 11:238, (1995). Sequencing is carried out as in EXAMPLE 1 using a blood sample from the patient in question. However, the BRCA $^{(omi)}$ (SEQ ID NO: 1) sequence is used for reference and polymorphic sites are compared to the nucleic acid sequences listed above for normal codons at each polymophic site. A normal sample is one which compares to the BRCA1$^{(omi)}$ sequence and contains one of the normal base variations which occur at each of the polymorphic sites. The codons which occur at each of the polymorphic sites are paired bellow.

AGC and AGT at position 2201,

TTG and CTG at position 2430,

CCG and CTG at position 2731,

GAA and GGA at position 3232,

AAA and AGA at position 3667,

TCT and TCC at position 4427, and

AGT and GGT at position 4956.

The availability of these polymorphic pairs provides added assurance that one skilled in the art can correctly interpret the polymorphic variations without mistaking a normal variation for a mutation.

As evident from the data in Table III and IV, the statistical analysis (on average) shows one or more normal codon pairs wherein the codons occur in the following frequencies in the normal population, respectively:

at position 2201, AGC and AGT occur at frequencies of about 40%, and from about 55–65%, respectively;

at position 2430, TTG and CTG occur at frequencies from about 35–45%, and from about 55–65%, respectively;

at position 2731, CCG and CTG occur at frequencies from about 25–35%, and from about 65–75%, respectively;

at position 3232, GAA and GGA occur at frequencies from about 35–45%, and from about 55–65%, respectively;

at position 3667, AAA and AGA occur at frequencies from about 35–45%, and from about 55–65%, respectively;

at position 4427, TCT and TCC occur at frequencies from about 45–55%, and from about 45–55%, respectively; and at position 4956, AGT and GGT occur at frequencies from about 35–45%, and from about 55–65%, respectively.

Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the Taq Dye Terminator Kit (PERKIN-ELMER® cat# 401628). DNA sequencing is performed in both forward and reverse directions on an Applied Biosystems, Inc. (ABI) automated sequencer (Model 377) The software used for analysis of the resulting data is "SEQUENCE NAVIGATOR®" purchased through ABI.

1. Polymerase Chain Reaction (PCR) Amplification

Genomic DNA (100 nanograms) extracted from white blood cells of the subject is amplified in a final volume of 25 microliters containing 1 microliter (100 nanograms) genomic DNA, 2.5 microliters 10X PCR buffer (100 mM Tris, pH 8.3, mM KCl, 1.2 mM MgCl$_2$), 2.5 microliters 10X dNTP mix (2 mM each nucleotide), 2.5 microliters forward primer (BRCA1-11K-F, 10 micromolar solution), 2.5 microliters reverse primer (BRCA1-11K-R, 10 micromolar solution),and 1 microliter Taq polymerase (5 units), and 13 microliters of water. The PCR primers used to amplify a patient's sample BRCA1 gene are listed in Table II. The primers were synthesized on an DNA/RNA Synthesizer Model 394®. Thirty-five cycles are of amplification are performed, each consisting of denaturing (95° C. 30 seconds), annealing (55° C. 1 minute), and extension (72° C.; 90 seconds), except during the first cycle in which the denaturing time is increased to 5 minutes, and during the last cycle in which the extension time is increased to 5 minutes.

PCR products are purified using QIA-QUICK® PCR purification kits (QIAGEN®, cat# 28104; Chatsworth, Calif.). Yield and purity of the PCR product determined spectrophotometrically at OD$_{260}$ on a Beckman DU 650 spectrophotometer.

2. Dideoxy Sequence Analysis

Fluorescent dye is attached to PCR products for automated sequencing using the Taq Dye Terminator Kit (PERKIN-ELMER® cat# 401628). DNA sequencing is performed in both forward and reverse directions on an Applied Biosystems, Inc. (ABI) Foster City, Calif., automated sequencer (Model 377). The software used for analysis of the resulting data is "SEQUENCE NAVIGATOR®" purchased through ABI. The BRCA1$^{(omi)}$ sequence (SEQ ID. NO: 1) is entered into the Sequence Navigator software as the Standard for comparison. The Sequence Navigator software compares the sample sequence to the BRCA1$^{(omi)}$ standard (SEQ ID NO: 1), base by base. The Sequence Navigator highlights all differences between the BRCA1 $^{(omi)}$ consensus normal DNA sequence and the patient's sample sequence.

A first technologist checks the computerized results by comparing visually the BRCA1$^{(omi)}$ standard (SEQ ID. NO: 1) against the patient's sample, and again highlights any differences between the standard and the sample. The first primary technologist then interprets the sequence variations at each position along the sequence. Chromatograms from each sequence variation are generated by the Sequence Navigator and printed on a color printer. The peaks are interpreted by the first primary technologist and also by a second primary technologist. A secondary technologist then reviews the chromatograms. The results are finally interpreted by a geneticist. In each instance, a variation is compared to known normal polymorphisms for position and base change. If the sample BRCA1 sequence matches the BRCA1$^{(omi)}$ standard, with only variations within the known list of polymorphisms, it is interpreted as a normal gene sequence. Mutations are noted by the length of non-matching variation. Such a lengthy mismatch pattern occurs with deletions and substitutions. An alteration such as a base substitution at a single position will be noted as a single mismatch between the standard and the patient's gene sample.

EXAMPLE 4

Determining the Presence of a Mutation in the BRCA1 Gene Using BRCA1$^{(omi)}$ and Seven Polymorphisms for Reference A person skilled in the art of genetic susceptibility testing will find the present invention useful for determining the presence of a known or previously unknown mutation in the BRCA1 gene. A list of mutations of BRCA1 is publicly available in the Breast Cancer Information Core at: http://www.nchgr.nih.gov/dir/lab_transfer/bic. This data site became publicly available on Nov. 1, 1995. Friend, S. et al. *Nature Genetics* 11:238, (1995). In this example, a mutation in exon 11 is characterized by amplifying the region of the mutation with a primer which matches the region of the mutation. Exon 11 of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached for automated sequencing using the Taq Dye Terminator Kit (Perkin-Elmer® cat# 401628). DNA sequencing is performed in both forward and reverse directions on an Applied Biosystems, Inc. (ABI) automated sequencer (Model 377). The software used for analysis of the resulting data is "Sequence Navigator" purchased through ABI. 1. Polymerase Chain Reaction (PCR) Amplification Genomic DNA (100 nanograms) extracted from white blood cells of the subject is amplified in a final volume of 25 microliters containing 1 microliter (100 nanograms) genomic DNA, 2.5 microliters 10X PCR buffer (100 mM Tris, pH 8.3, 500 mM KCl, 1.2 mM MgCl$^2$), 2.5 microliters 10X dNTP mix (2 mM each nucleotide), 2.5 microliters forward primer (BRCA1-11K-F, 10 micromolar solution), 2.5 microliters reverse primer (BRCA1-11K-R, 10 micromolar solution), and 1 microliter Taq polymerase (5 units), and 13 microliters of water. The PCR primers used to amplify segment K of exon 11 (where the mutation is found) are as follows:

BRCA1-11K-F: 5'-GCA AAA GCG TCC AGA AAG GA-3' SEQ ID NO: 69

BRCA1-11K-R: 5'-AGT CTT CCA ATT CAC TGC AC-3' SEQ ID NO: 70

The primers are synthesized on an DNA/RNA Synthesizer Model 394®. Thirty-five cycles are performed, each consisting of denaturing (95° C. 30 seconds), annealing (55° C.; 1 minute), and extension (72° C.; 90 seconds), except during the first cycle in which the denaturing time is increased to 5 minutes, and during the last cycle in which the extension time is increased to 5 minutes. PCR products are purified using QIA-QUICK® PCR purification kits (Qiagen®, cat# 28104; Chatsworth, Calif.). Yield and purity of the PCR product determined spectrophotometrically at OD$_{260}$ on a Beckman DU 650 spectrophotometer.

2. Dideoxy Sequence Analysis

Fluorescent dye is attached to PCR products for automated sequencing using the Taq Dye Terminator Kit (PERKIN-ELMER® Cat # 401628). DNA sequencing is performed in both forward and reverse directions on an Applied Biosystems, Inc. (ABI) Foster City, Calif., automated sequencer (Model 377). The software used for analysis of the resulting data is "SEQUENCE NAVIGATOR" purchased through ABI. The BRCA1$^{(omi)}$ sequence is entered into the SEQUENCE Navigator software as the Standard for comparison. The Sequence Navigator software compares the sample sequence to the BRCA1$^{(omi)}$ standard (SEQ ID. NO: 1), base by base. The Sequence Navigator highlights all differences between the BRCA1$^{(omi)}$ (SEQ ID. NO: 1) consensus normal DNA sequence and the patient's sample sequence.

A first technologist checks the computerized results by comparing visually the BRCA1$^{(omi)}$ standard against the patient's sample, and again highlights any differences between the standard and the sample. The first primary technologist then interprets the sequence variations at each position along the sequence. Chromatograms from each sequence variation are generated by the Sequence Navigator and printed on a color printer. The peaks are interpreted by the first primary technologist and a second primary technologist. A secondary technologist then reviews the chromatograms. The results are finally interpreted by a geneticist. In each instance, a variation is compared to known normal polymorphisms for position and base change. The seven known polymorphisms which occur in the Consensus Normal DNA sequence are:

AGC and AGT at position 2201,

TTG and CTG at position 2430,

CCG and CTG at position 2731,

GAA and GGA at position 3232,

AAA and AGA at position 3667,

TCT and TCC at position 4427, and

AGT and GGT at position 4956.

Mutations are noted by the length of non-matching variation. Such a lengthy mismatch pattern occurs with deletions and substitutions.

5. Result

Using the above PCR amplification and standard fluorescent sequencing technology, The 3888delGA mutation may be found. The 3888delGA mutation The BRCA1 gene lies in segment "K" of exon 11. The DNA sequence results demonstrate the presence of a two base pair deletion at nucleotides 3888 and 3889 of the published BRCA1$^{(omi)}$ sequence. This mutation interrupts the normal reading frame of the BRCA1 transcript, resulting in the appearance of an in-frame terminator (TAG) at codon position 1265. This mutation is, therefore, predicted to result in a truncated, and most likely, non-functional protein. The formal name of the mutation will be 3888delGA. This mutation is named in accordance with the suggested nomenclature for naming mutations, Baudet, A et al., *Human Mutation* 2:245–248, (1993).

TABLE OF REFERENCES

1. Sanger, F., et al., J. Mol. Biol. 42:1617, (1980).
2. Beaucage, et al., Tetrahedron Letters 22:1859–1862, (1981).
3. Maniatis, et. al. in Molecular Cloning: A Laboratory Manual, Cold Spring Harbor, NY, p 280–281, (1982).
4. Conner, et. al., Proc. Natl. Acad. Sci. U.S.A. 80:278, (1983)
5. Saiki, et. al., Bio/Technology 3:1008–1012, (1985)

TABLE OF REFERENCES

6. Landgren, et. al., Science 241:1007, (1988)
7. Landgren, et. al., Science 242:229–237, (1988).
8. PCR. A Practical Approach, ILR Press, Eds. M. J. McPherson, P. Quirke, and G. R. Taylor, (1992).
9. Easton et al., American Journal of Human Genetics 52:678–701, (1993).
10. U.S. Pat. No. 4,458,066.
11. Rowell, S., et al., American Journal of Human Genetics 55:861–865, (1994)
12. Miki, Y. et al., Science 266:66–71, (1994).
13. Friedman, L. et al., Nature Genetics 8:399–404, (1994).
14. Baudet, A et al., Human Mutation 2:245–248, (1993).
15. Friend, S. et al. Nature Genetics 11:238, (1995).

Although the invention has been described with reference to the presently preferred embodiments, it should be understood that various modifications can be made without departing from the spirit of the invention. Accordingly, the invention is limited only by the following claims.

We claim:

1. An isolated consensus DNA sequence of the BRCA1 coding sequence as set forth in SEQ ID NO: 1.

2. A method of identifying individuals having a BRCA1 gene with a BRCA1 coding sequence not associated with breast or ovarian cancer comprising:

a) amplifying a DNA fragment of an individual's BRCA1 coding sequence using an oligonucleotide primer which specifically hybridizes to sequences within the gene;

b) sequencing said amplified fragment by dideoxy sequencing;

c) repeating steps (a) and (b) until said individual's BRCA1 coding sequence is completely sequenced;

d) comparing the sequence of said amplified DNA to the sequence of SEQ. ID. NO: 1;

e) determining the presence or absence of each of the following polymorphic variations in said individual's BRCA1 coding sequence:
    AGC and ACT at position 2201,
    TTG and CTG at position 2430,
    CCG and CTG at position 2731,
    GAA and GGA at position 3232,
    AAA and AGA at position 3667,
    TCT and TCC at position 4427,
    and ACT and GGT at position 4956;

f) determining any sequence differences between said individual's BRCA1 coding sequences and SEQ. ID. NO: 1 wherein the presence of any of the said polymorphic variations and the absence of a polymorphism outside of positions 2201, 2430, 2731, 3232, 3667, 4427, and 4956, is correlated with an absence of increased genetic susceptibility to breast or ovarian cancer resulting from a BRCA1 mutation in the BRCA1 coding sequence.

3. A method according to claim 2 wherein said oligonucleotide primer is labeled with a radiolabel, a fluorescent label, a bioluminescent label, a chemiluminescent label or an enzyme label.

4. A method of detecting an increased genetic susceptibility to breast and ovarian cancer in an individual resulting from the presence of a mutation in the BRCA1 coding sequence, comprising:

a) amplifying a DNA fragment of an individual's BRCA1 coding sequence using an oligonucleotide primer which specifically hybridizes to sequences within the gene;

b) sequencing said amplified fragment by dideoxy sequencing;

c) repeating steps (a) and (b) until said individual's BRCA1 coding sequence is completely sequenced;

d) comparing the sequence of said amplified DNA to the sequence of SEQ. ID. NO: 1;

e) determining any sequence differences between said individual's BRCA1 coding sequences and SEQ. ID. NO: 1 to determine the presence or absence of polymorphisms in said individual's BRCA coding sequences wherein a polymorphism which is not any of the following:

AGC or AGT at position 2201,
TTG or CTG at position 2430,
CCG or CTG at position 2731,
GAA or GGA at position 3232,
AAA or AGA at position 3667,
TCT or TCC at position 4427,
and AGT or GGT at position 4956;

is correlated with the potential of increased genetic susceptibility to breast or ovarian cancer resulting from a BRCA1 mutation in the BRCA1 coding sequence.

* * * * *

UNITED STATES PATENT AND TRADEMARK OFFICE
CERTIFICATE OF CORRECTION

PATENT NO. : 5,654,155
DATED : August 5, 1997
INVENTOR(S) : Brenda S. Critz, et al It is certified that error appears in the above-identified patent and that said Letters Patent is hereby corrected as shown below:

Column 15, line 34, replace "bellow" with --below--;

Column 18, line 57, replace "Baudet" with --Beaudet--;

Column 20, line 5, replace "Baudet" with --Beaudet--;

Signed and Sealed this

Twenty-eighth Day of April, 1998

Attest:

BRUCE LEHMAN

Attesting Officer

Commissioner of Patents and Trademarks

UNITED STATES PATENT AND TRADEMARK OFFICE
CERTIFICATE OF CORRECTION

| | | |
|---|---|---|
| PATENT NO. | : 5,654,155 | Page 1 of 1 |
| APPLICATION NO. | : 08/598591 | |
| DATED | : August 5, 1997 | |
| INVENTOR(S) | : Patricia D. Murphy et al. | |

It is certified that error appears in the above-identified patent and that said Letters Patent is hereby corrected as shown below:

Column 66, line 44 (Claim 2) – please replace "ACT" with --AGT--

Signed and Sealed this

Thirtieth Day of January, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 5,654,155 |
| APPLICATION NO. | : 08/598591 |
| DATED | : August 5, 1997 |
| INVENTOR(S) | : Patricia D. Murphy et al. |

It is certified that error appears in the above-identified patent and that said Letters Patent is hereby corrected as shown below:

Column 65, line 63 (Claim 2) - please replace "ACT" with --AGT--

Signed and Sealed this

Twenty-eighth Day of October, 2008

JON W. DUDAS
*Director of the United States Patent and Trademark Office*

SEQUENCE LISTING ( 1 ) GENERAL INFORMATION:

( i i i ) NUMBER OF SEQUENCES: 74

( 2 ) INFORMATION FOR SEQ ID NO:1:

( i ) SEQUENCE CHARACTERISTICS:
        ( A ) LENGTH: 5711 base pairs
        ( B ) TYPE: nucleic acid
        ( C ) STRANDEDNESS: Not Relevant
        ( D ) TOPOLOGY: linear ( i i ) MOLECULE TYPE: cDNA ( v i ) ORIGINAL SOURCE:
        ( A ) ORGANISM: Homo sapiens
        ( B ) STRAIN: BRCA1

( v i i i ) POSITION IN GENOME:
        ( A ) CHROMOSOME/SEGMENT: 17
        ( B ) MAP POSITION: 17q21

( x i ) SEQUENCE DESCRIPTION: SEQ ID NO:1:

```
AGCTCGCTGA GACTTCCTGG ACCCGCACC  AGGCTGTGGG GTTTCTCAGA TAACTGGGCC        60
CCTGCGCTCA GGAGGCCTTC ACCCTCTGCT CTGGGTAAAG TTCATTGGAA CAGAAAGAAA       120
TGGATTTATC TGCTCTTCGC GTTGAAGAAG TACAAAATGT CATTAATGCT ATGCAGAAAA       180
TCTTAGAGTG TCCCATCTGT CTGGAGTTGA TCAAGGAACC TGTCTCCACA AAGTGTGACC       240
ACATATTTTG CAAATTTTGC ATGCTGAAAC TTCTCAACCA GAAGAAAGGG CCTTCACAGT       300
GTCCTTTATG TAAGAATGAT ATAACCAAAA GGAGCCTACA AGAAAGTACG AGATTTAGTC       360
AACTTGTTGA AGAGCTATTG AAAATCATTT GTGCTTTTCA GCTTGACACA GGTTTGGAGT       420
ATGCAAACAG CTATAATTTT GCAAAAAAGG AAAATAACTC TCCTGAACAT CTAAAAGATG       480
AAGTTTCTAT CATCCAAAGT ATGGGCTACA GAAACCGTGC CAAAAGACTT CTACAGAGTG       540
AACCCGAAAA TCCTTCCTTG CAGGAAACCA GTCTCAGTGT CCAACTCTCT AACCTTGGAA       600
CTGTGAGAAC TCTGAGGACA AAGCAGCGGA TACAACCTCA AAAGACGTCT GTCTACATTG       660
AATTGGGATC TGATTCTTCT GAAGATACCG TTAATAAGGC AACTTATTGC AGTGTGGGAG       720
ATCAAGAATT GTTACAAATC ACCCCTCAAG GAACCAGGGA TGAAATCAGT TTGGATTCTG       780
CAAAAAAGGC TGCTTGTGAA TTTTCTGAGA CGGATGTAAC AAATACTGAA CATCATCAAC       840
CCAGTAATAA TGATTTGAAC ACCACTGAGA AGCGTGCAGC TGAGAGGCAT CCAGAAAAGT       900
ATCAGGGTAG TTCTGTTTCA AACTTGCATG TGGAGCCATG TGGCACAAAT ACTCATGCCA       960
GCTCATTACA GCATGAGAAC AGCAGTTTAT TACTCACTAA AGACAGAATG AATGTAGAA      1020
```

```
AGGCTGAATT CTGTAATAAA AGCAAACAGC CTGGCTTAGC AAGGAGCCAA CATAACAGAT    1080
GGGCTGGAAG TAAGGAAACA TGTAATGATA GGCGGACTCC CAGCACAGAA AAAAAGGTAG    1140
ATCTGAATGC TGATCCCCTG TGTGAGAGAA AGAATGGAA TAAGCAGAAA CTGCCATGCT     1200
CAGAGAATCC TAGAGATACT GAAGATGTTC CTTGGATAAC ACTAAATAGC AGCATTCAGA    1260
AAGTTAATGA GTGGTTTTCC AGAAGTGATG AACTGTTAGG TTCTGATGAC TCACATGATG    1320
GGGAGTCTGA ATCAAATGCC AAAGTAGCTG ATGTATTGGA CGTTCTAAAT GAGGTAGATG    1380
AATATTCTGG TTCTTCAGAG AAAATAGACT TACTGGCCAG TGATCCTCAT GAGGCTTTAA    1440
TATGTAAAAG TGAAAGAGTT CACTCCAAAT CAGTAGAGAG TAATATTGAA GACAAAATAT    1500
TTGGGAAAAC CTATCGGAAG AAGGCAAGCC TCCCCAACTT AAGCCATGTA ACTGAAAATC    1560
TAATTATAGG AGCATTTGTT ACTGAGCCAC AGATAATACA AGAGCGTCCC CTCACAAATA    1620
AATTAAAGCG TAAAAGGAGA CCTACATCAG GCCTTCATCC TGAGGATTTT ATCAAGAAAG    1680
CAGATTTGGC AGTTCAAAAG ACTCCTGAAA TGATAAATCA GGGAACTAAC CAAACGGAGC    1740
AGAATGGTCA AGTGATGAAT ATTACTAATA GTGGTCATGA GAATAAAACA AAGGTGATT    1800
CTATTCAGAA TGAGAAAAAT CCTAACCCAA TAGAATCACT CGAAAAAGAA TCTGCTTTCA    1860
AAACGAAAGC TGAACCTATA AGCAGCAGTA TAAGCAATAT GGAACTCGAA TTAAATATCC    1920
ACAATTCAAA AGCACCTAAA AAGAATAGGC TGAGGAGGAA GTCTTCTACC AGGCATATTC    1980
ATGCGCTTGA ACTAGTAGTC AGTAGAAATC TAAGCCCACC TAATTGTACT GAATTGCAAA    2040
TTGATAGTTG TTCTAGCAGT GAAGAGATAA AGAAAAAAA GTACAACCAA ATGCCAGTCA     2100
GGCACAGCAG AAACCTACAA CTCATGGAAG GTAAAGAACC TGCAACTGGA GCCAAGAAGA    2160
GTAACAAGCC AAATGAACAG ACAAGTAAAA GACATGACAG TGATACTTTC CCAGAGCTGA    2220
AGTTAACAAA TGCACCTGGT TCTTTTACTA AGTGTTCAAA TACCAGTGAA CTTAAAGAAT    2280
TTGTCAATCC TAGCCTTCCA AGAGAAGAAA AAGAAGAGAA ACTAGAAACA GTTAAAGTGT    2340
CTAATAATGC TGAAGACCCC AAAGATCTCA TGTTAAGTGG AGAAAGGGTT TTGCAAACTG    2400
AAAGATCTGT AGAGAGTAGC AGTATTTCAC TGGTACCTGG TACTGATTAT GGCACTCAGG    2460
AAAGTATCTC GTTACTGGAA GTTAGCACTC TAGGGAAGGC AAAAACAGAA CCAAATAAAT    2520
GTGTGAGTCA GTGTGCAGCA TTTGAAAACC CCAAGGGACT AATTCATGGT TGTTCCAAAG    2580
ATAATAGAAA TGACACAGAA GGCTTTAAGT ATCCATTGGG ACATGAAGTT AACCACAGTC    2640
GGGAAACAAG CATAGAAATG GAAGAAAGTG AACTTGATGC TCAGTATTTG CAGAATACAT    2700
TCAAGGTTTC AAAGCGCCAG TCATTTGCTC TGTTTTCAAA TCCAGGAAAT GCAGAAGAGG    2760
AATGTGCAAC ATTCTCTGCC CACTCTGGGT CCTTAAAGAA ACAAAGTCCA AAAGTCACTT    2820
TTGAATGTGA ACAAAAGGAA GAAAATCAAG GAAGAATGA GTCTAATATC AAGCCTGTAC     2880
AGACAGTTAA TATCACTGCA GGCTTTCCTG TGGTTGGTCA GAAAGATAAG CCAGTTGATA    2940
ATGCCAAATG TAGTATCAAA GGAGGCTCTA GGTTTTGTCT ATCATCTCAG TTCAGAGGCA    3000
ACGAAACTGG ACTCATTACT CCAAATAAAC ATGGACTTTT ACAAAACCCA TATCGTATAC    3060
CACCACTTTT TCCCATCAAG TCATTTGTTA AAACTAAATG TAAGAAAAAT CTGCTAGAGG    3120
AAAACTTTGA GGAACATTCA ATGTCACCTG AAAGAGAAAT GGGAAATGAG AACATTCCAA    3180
GTACAGTGAG CACAATTAGC CGTAATAACA TTAGAGAAAA TGTTTTTAAA GGAGCCAGCT    3240
CAAGCAATAT TAATGAAGTA GGTTCCAGTA CTAATGAAGT GGGCTCCAGT ATTAATGAAA    3300
TAGGTTCCAG TGATGAAAAC ATTCAAGCAG AACTAGGTAG AAACAGAGGG CCAAAATTGA    3360
ATGCTATGCT TAGATTAGGG GTTTTGCAAC CTGAGGTCTA TAAACAAAGT CTTCCTGGAA    3420
```

-continued

```
GTAATTGTAA GCATCCTGAA ATAAAAAAGC AAGAATATGA AGAAGTAGTT CAGACTGTTA    3480
ATACAGATTT CTCTCCATAT CTGATTTCAG ATAACTTAGA ACAGCCTATG GGAAGTAGTC    3540
ATGCATCTCA GGTTTGTTCT GAGACACCTG ATGACCTGTT AGATGATGGT GAAATAAAGG    3600
AAGATACTAG TTTTGCTGAA AATGACATTA AGGAAAGTTC TGCTGTTTTT AGCAAAAGCG    3660
TCCAGAGAGG AGAGCTTAGC AGGAGTCCTA GCCCTTTCAC CCATACACAT TTGGCTCAGG    3720
GTTACCGAAG AGGGGCCAAG AAATTAGAGT CCTCAGAAGA GAACTTATCT AGTGAGGATG    3780
AAGAGCTTCC CTGCTTCCAA CACTTGTTAT TTGGTAAAGT AAACAATATA CCTTCTCAGT    3840
CTACTAGGCA TAGCACCGTT GCTACCGAGT GTCTGTCTAA GAACACAGAG GAGAATTTAT    3900
TATCATTGAA GAATAGCTTA AATGACTGCA GTAACCAGGT AATATTGGCA AAGGCATCTC    3960
AGGAACATCA CCTTAGTGAG GAAACAAAAT GTTCTGCTAG CTTGTTTTCT TCACAGTGCA    4020
GTGAATTGGA AGACTTGACT GCAAATACAA ACACCCAGGA TCCTTTCTTG ATTGGTTCTT    4080
CCAAACAAAT GAGGCATCAG TCTGAAAGCC AGGGAGTTGG TCTGAGTGAC AAGGAATTGG    4140
TTTCAGATGA TGAAGAAAGA GGAACGGGCT TGGAAGAAAA TAATCAAGAA GAGCAAAGCA    4200
TGGATTCAAA CTTAGGTGAA GCAGCATCTG GGTGTGAGAG TGAAACAAGC GTCTCTGAAG    4260
ACTGCTCAGG GCTATCCTCT CAGAGTGACA TTTTAACCAC TCAGCAGAGG GATACCATGC    4320
AACATAACCT GATAAAGCTC CAGCAGGAAA TGGCTGAACT AGAAGCTGTG TTAGAACAGC    4380
ATGGGAGCCA GCCTTCTAAC AGCTACCCTT CCATCATAAG TGACTCCTCT GCCCTTGAGG    4440
ACCTGCGAAA TCCAGAACAA AGCACATCAG AAAAAGCAGT ATTAACTTCA CAGAAAGTA     4500
GTGAATACCC TATAAGCCAG AATCCAGAAG GCCTTTCTGC TGACAAGTTT GAGGTGTCTG    4560
CAGATAGTTC TACCAGTAAA AATAAAGAAC CAGGAGTGGA AAGGTCATCC CCTTCTAAAT    4620
GCCCATCATT AGATGATAGG TGGTACATGC ACAGTTGCTC TGGGAGTCTT CAGAATAGAA    4680
ACTACCCATC TCAAGAGGAG CTCATTAAGG TTGTTGATGT GGAGGAGCAA CAGCTGGAAG    4740
AGTCTGGGCC ACACGATTTG ACGGAAACAT CTTACTTGCC AAGGCAAGAT CTAGAGGGAA    4800
CCCCTTACCT GGAATCTGGA ATCAGCCTCT TCTCTGATGA CCCTGAATCT GATCCTTCTG    4860
AAGACAGAGC CCCAGAGTCA GCTCGTGTTG GCAACATACC ATCTTCAACC TCTGCATTGA    4920
AGTTCCCCA ATTGAAAGTT GCAGAATCTG CCCAGGGTCC AGCTGCTGCT CATACTACTG    4980
ATACTGCTGG GTATAATGCA ATGGAAGAAA GTGTGAGCAG GGAGAAGCCA GAATTGACAG    5040
CTTCAACAGA AAGGGTCAAC AAAAGAATGT CCATGGTGGT GTCTGGCCTG ACCCCAGAAG    5100
AATTTATGCT CGTGTACAAG TTTGCCAGAA ACACCACAT CACTTTAACT AATCTAATTA     5160
CTGAAGAGAC TACTCATGTT GTTATGAAAA CAGATGCTGA GTTTGTGTGT AACGGACAC     5220
TGAAATATTT TCTAGGAATT GCGGGAGGAA AATGGGTAGT TAGCTATTTC TGGGTGACCC    5280
AGTCTATTAA AGAAAGAAAA ATGCTGAATG AGCATGATTT TGAAGTCAGA GGAGATGTGG    5340
TCAATGGAAG AAACCACCAA GGTCCAAAGC GAGCAAGAGA ATCCCAGGAC AGAAAGATCT    5400
TCAGGGGCT AGAAATCTGT TGCTATGGGC CCTTCACCAA CATGCCCACA GATCAACTGG     5460
AATGGATGGT ACAGCTGTGT GGTGCTTCTG TGGTGAAGGA GCTTTCATCA TTCACCCTTG    5520
GCACAGGTGT CCACCCAATT GTGGTTGTGC AGCCAGATGC CTGGACAGAG GACAATGGCT    5580
TCCATGCAAT TGGGCAGATG TGTGAGGCAC CTGTGGTGAC CCGAGAGTGG GTGTTGGACA    5640
GTGTAGCACT CTACCAGTGC CAGGAGCTGG ACACCTACCT GATACCCAG ATCCCCCACA     5700
GCCACTACTG A                                                        5711
```

( 2 ) INFORMATION FOR SEQ ID NO:2:

( i ) SEQUENCE CHARACTERISTICS:
        ( A ) LENGTH: 1863 amino acids
        ( B ) TYPE: amino acid
        ( C ) STRANDEDNESS: Not Relevant
        ( D ) TOPOLOGY: Not Relevant ( i i ) MOLECULE TYPE: protein ( v i ) ORIGINAL SOURCE:
        ( A ) ORGANISM: Homo sapiens
        ( B ) STRAIN: BRCA1

( v i i i ) POSITION IN GENOME:
        ( A ) CHROMOSOME/SEGMENT: 17
        ( B ) MAP POSITION: 17q21

( x i ) SEQUENCE DESCRIPTION: SEQ ID NO:2:

```
Met Asp Leu Ser Ala Leu Arg Val Glu Glu Val Gln Asn Val Ile Asn
 1               5                  10                  15
Ala Met Gln Lys Ile Leu Glu Cys Pro Ile Cys Leu Glu Leu Ile Lys
             20                  25                  30
Glu Pro Val Ser Thr Lys Cys Asp His Ile Phe Cys Lys Phe Cys Met
         35                  40                  45
Leu Lys Leu Leu Asn Gln Lys Lys Gly Pro Ser Gln Cys Pro Leu Cys
     50                  55                  60
Lys Asn Asp Ile Thr Lys Arg Ser Leu Gln Glu Ser Thr Arg Phe Ser
 65                  70                  75                  80
Gln Leu Val Glu Glu Leu Leu Lys Ile Ile Cys Ala Phe Gln Leu Asp
                 85                  90                  95
Thr Gly Leu Glu Tyr Ala Asn Ser Tyr Asn Phe Ala Lys Lys Glu Asn
            100                 105                 110
Asn Ser Pro Glu His Leu Lys Asp Glu Val Ser Ile Ile Gln Ser Met
        115                 120                 125
Gly Tyr Arg Asn Arg Ala Lys Arg Leu Leu Gln Ser Glu Pro Glu Asn
    130                 135                 140
Pro Ser Leu Gln Glu Thr Ser Leu Ser Val Gln Leu Ser Asn Leu Gly
145                 150                 155                 160
Thr Val Arg Thr Leu Arg Thr Lys Gln Arg Ile Gln Pro Gln Lys Thr
                165                 170                 175
Ser Val Tyr Ile Glu Leu Gly Ser Asp Ser Ser Glu Asp Thr Val Asn
            180                 185                 190
Lys Ala Thr Tyr Cys Ser Val Gly Asp Gln Glu Leu Leu Gln Ile Thr
        195                 200                 205
Pro Gln Gly Thr Arg Asp Glu Ile Ser Leu Asp Ser Ala Lys Lys Ala
    210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
        275                 280                 285
Ser Leu Leu Leu Thr Lys Asp Arg Met Asn Val Glu Lys Ala Glu Phe
    290                 295                 300
Cys Asn Lys Ser Lys Gln Pro Gly Leu Ala Arg Ser Gln His Asn Arg
305                 310                 315                 320
```

```
Trp Ala Gly Ser Lys Glu Thr Cys Asn Asp Arg Arg Thr Pro Ser Thr
            325                 330                 335
Glu Lys Lys Val Asp Leu Asn Ala Asp Pro Leu Cys Glu Arg Lys Glu
            340             345             350
Trp Asn Lys Gln Lys Leu Pro Cys Ser Glu Asn Pro Arg Asp Thr Glu
        355                 360                 365
Asp Val Pro Trp Ile Thr Leu Asn Ser Ser Ile Gln Lys Val Asn Glu
370                 375                 380
Trp Phe Ser Arg Ser Asp Glu Leu Leu Gly Ser Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
        435                 440                 445
Ser Lys Ser Val Glu Ser Asn Ile Glu Asp Lys Ile Phe Gly Lys Thr
    450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
        515                 520                 525
Pro Glu Met Ile Asn Gln Gly Thr Asn Gln Thr Glu Gln Asn Gly Gln
    530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Lys Thr Lys Ala Glu Pro Ile Ser Ser Ser Ile Ser
            580                 585                 590
Asn Met Glu Leu Glu Leu Asn Ile His Asn Ser Lys Ala Pro Lys Lys
        595                 600                 605
Asn Arg Leu Arg Arg Lys Ser Ser Thr Arg His Ile His Ala Leu Glu
    610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Lys Tyr Asn
                645                 650                 655
Gln Met Pro Val Arg His Ser Arg Asn Leu Gln Leu Met Glu Gly Lys
            660                 665                 670
Glu Pro Ala Thr Gly Ala Lys Lys Ser Asn Lys Pro Asn Glu Gln Thr
        675                 680                 685
Ser Lys Arg His Asp Ser Asp Thr Phe Pro Glu Leu Lys Leu Thr Asn
    690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
                725                 730                 735
Thr Val Lys Val Ser Asn Asn Ala Glu Asp Pro Lys Asp Leu Met Leu
            740                 745                 750
```

```
Ser  Gly  Glu  Arg  Val  Leu  Gln  Thr  Glu  Arg  Ser  Val  Glu  Ser  Ser  Ser
          755                 760                 765

Ile  Ser  Leu  Val  Pro  Gly  Thr  Asp  Tyr  Gly  Thr  Gln  Glu  Ser  Ile  Ser
          770                 775                 780

Leu  Leu  Glu  Val  Ser  Thr  Leu  Gly  Lys  Ala  Lys  Thr  Glu  Pro  Asn  Lys
785                      790                 795                           800

Cys  Val  Ser  Gln  Cys  Ala  Ala  Phe  Glu  Asn  Pro  Lys  Gly  Leu  Ile  His
                    805                 810                           815

Gly  Cys  Ser  Lys  Asp  Asn  Arg  Asn  Asp  Thr  Glu  Gly  Phe  Lys  Tyr  Pro
               820                      825                      830

Leu  Gly  His  Glu  Val  Asn  His  Ser  Arg  Glu  Thr  Ser  Ile  Glu  Met  Glu
          835                      840                      845

Glu  Ser  Glu  Leu  Asp  Ala  Gln  Tyr  Leu  Gln  Asn  Thr  Phe  Lys  Val  Ser
     850                      855                      860

Lys  Arg  Gln  Ser  Phe  Ala  Leu  Phe  Ser  Asn  Pro  Gly  Asn  Ala  Glu  Glu
865                      870                 875                           880

Glu  Cys  Ala  Thr  Phe  Ser  Ala  His  Ser  Gly  Ser  Leu  Lys  Lys  Gln  Ser
                    885                 890                           895

Pro  Lys  Val  Thr  Phe  Glu  Cys  Glu  Gln  Lys  Glu  Glu  Asn  Gln  Gly  Lys
                    900                 905                      910

Asn  Glu  Ser  Asn  Ile  Lys  Pro  Val  Gln  Thr  Val  Asn  Ile  Thr  Ala  Gly
               915                 920                 925

Phe  Pro  Val  Val  Gly  Gln  Lys  Asp  Lys  Pro  Val  Asp  Asn  Ala  Lys  Cys
     930                      935                 940

Ser  Ile  Lys  Gly  Gly  Ser  Arg  Phe  Cys  Leu  Ser  Ser  Gln  Phe  Arg  Gly
945                      950                 955                           960

Asn  Glu  Thr  Gly  Leu  Ile  Thr  Pro  Asn  Lys  His  Gly  Leu  Leu  Gln  Asn
                    965                 970                           975

Pro  Tyr  Arg  Ile  Pro  Pro  Leu  Phe  Pro  Ile  Lys  Ser  Phe  Val  Lys  Thr
               980                 985                      990

Lys  Cys  Lys  Lys  Asn  Leu  Leu  Glu  Glu  Asn  Phe  Glu  Glu  His  Ser  Met
          995                 1000                1005

Ser  Pro  Glu  Arg  Glu  Met  Gly  Asn  Glu  Asn  Ile  Pro  Ser  Thr  Val  Ser
     1010                    1015                1020

Thr  Ile  Ser  Arg  Asn  Asn  Ile  Arg  Glu  Asn  Val  Phe  Lys  Gly  Ala  Ser
1025                    1030                1035                          1040

Ser  Ser  Asn  Ile  Asn  Glu  Val  Gly  Ser  Ser  Thr  Asn  Glu  Val  Gly  Ser
                    1045                1050                         1055

Ser  Ile  Asn  Glu  Ile  Gly  Ser  Ser  Asp  Glu  Asn  Ile  Gln  Ala  Glu  Leu
               1060                1065                      1070

Gly  Arg  Asn  Arg  Gly  Pro  Lys  Leu  Asn  Ala  Met  Leu  Arg  Leu  Gly  Val
          1075                    1080                1085

Leu  Gln  Pro  Glu  Val  Tyr  Lys  Gln  Ser  Leu  Pro  Gly  Ser  Asn  Cys  Lys
     1090                    1095                1100

His  Pro  Glu  Ile  Lys  Lys  Gln  Glu  Tyr  Glu  Glu  Val  Val  Gln  Thr  Val
1105                    1110                1115                          1120

Asn  Thr  Asp  Phe  Ser  Pro  Tyr  Leu  Ile  Ser  Asp  Asn  Leu  Glu  Gln  Pro
                    1125                1130                      1135

Met  Gly  Ser  Ser  His  Ala  Ser  Gln  Val  Cys  Ser  Glu  Thr  Pro  Asp  Asp
               1140                1145                      1150

Leu  Leu  Asp  Asp  Gly  Glu  Ile  Lys  Glu  Asp  Thr  Ser  Phe  Ala  Glu  Asn
          1155                1160                      1165

Asp  Ile  Lys  Glu  Ser  Ser  Ala  Val  Phe  Ser  Lys  Ser  Val  Gln  Arg  Gly
```

-continued

```
                     1170                      1175                          1180
        Glu  Leu  Ser  Arg  Ser  Pro  Ser  Pro  Phe  Thr  His  Thr  His  Leu  Ala  Gln
        1185                      1190                     1195                     1200

Gly  Tyr  Arg  Arg  Gly  Ala  Lys  Lys  Leu  Glu  Ser  Ser  Glu  Glu  Asn  Leu
                            1205                     1210                     1215

Ser  Ser  Glu  Asp  Glu  Glu  Leu  Pro  Cys  Phe  Gln  His  Leu  Leu  Phe  Gly
                            1220                     1225                     1230

Lys  Val  Asn  Asn  Ile  Pro  Ser  Gln  Ser  Thr  Arg  His  Ser  Thr  Val  Ala
                            1235                     1240                     1245

Thr  Glu  Cys  Leu  Ser  Lys  Asn  Thr  Glu  Glu  Asn  Leu  Leu  Ser  Leu  Lys
                            1250                     1255                     1260

Asn  Ser  Leu  Asn  Asp  Cys  Ser  Asn  Gln  Val  Ile  Leu  Ala  Lys  Ala  Ser
        1265                     1270                     1275                     1280

Gln  Glu  His  His  Leu  Ser  Glu  Glu  Thr  Lys  Cys  Ser  Ala  Ser  Leu  Phe
                            1285                     1290                     1295

Ser  Ser  Gln  Cys  Ser  Glu  Leu  Glu  Asp  Leu  Thr  Ala  Asn  Thr  Asn  Thr
                            1300                     1305                     1310

Gln  Asp  Pro  Phe  Leu  Ile  Gly  Ser  Ser  Lys  Gln  Met  Arg  His  Gln  Ser
                            1315                     1320                     1325

Glu  Ser  Gln  Gly  Val  Gly  Leu  Ser  Asp  Lys  Glu  Leu  Val  Ser  Asp  Asp
        1330                     1335                     1340

Glu  Glu  Arg  Gly  Thr  Gly  Leu  Glu  Glu  Asn  Asn  Gln  Glu  Glu  Gln  Ser
        1345                     1350                     1355                     1360

Met  Asp  Ser  Asn  Leu  Gly  Glu  Ala  Ala  Ser  Gly  Cys  Glu  Ser  Glu  Thr
                            1365                     1370                     1375

Ser  Val  Ser  Glu  Asp  Cys  Ser  Gly  Leu  Ser  Ser  Gln  Ser  Asp  Ile  Leu
                            1380                     1385                     1390

Thr  Thr  Gln  Gln  Arg  Asp  Thr  Met  Gln  His  Asn  Leu  Ile  Lys  Leu  Gln
                            1395                     1400                     1405

Gln  Glu  Met  Ala  Glu  Leu  Glu  Ala  Val  Leu  Glu  Gln  His  Gly  Ser  Gln
                            1410                     1415                     1420

Pro  Ser  Asn  Ser  Tyr  Pro  Ser  Ile  Ile  Ser  Asp  Ser  Ser  Ala  Leu  Glu
        1425                     1430                     1435                     1440

Asp  Leu  Arg  Asn  Pro  Glu  Gln  Ser  Thr  Ser  Glu  Lys  Ala  Val  Leu  Thr
                            1445                     1450                     1455

Ser  Gln  Lys  Ser  Ser  Glu  Tyr  Pro  Ile  Ser  Gln  Asn  Pro  Glu  Gly  Leu
                            1460                     1465                     1470

Ser  Ala  Asp  Lys  Phe  Glu  Val  Ser  Ala  Asp  Ser  Ser  Thr  Ser  Lys  Asn
                            1475                     1480                     1485

Lys  Glu  Pro  Gly  Val  Glu  Arg  Ser  Ser  Pro  Ser  Lys  Cys  Pro  Ser  Leu
                            1490                     1495                     1500

Asp  Asp  Arg  Trp  Tyr  Met  His  Ser  Cys  Ser  Gly  Ser  Leu  Gln  Asn  Arg
        1505                     1510                     1515                     1520

Asn  Tyr  Pro  Ser  Gln  Glu  Glu  Leu  Ile  Lys  Val  Val  Asp  Val  Glu  Glu
                            1525                     1530                     1535

Gln  Gln  Leu  Glu  Glu  Ser  Gly  Pro  His  Asp  Leu  Thr  Glu  Thr  Ser  Tyr
                            1540                     1545                     1550

Leu  Pro  Arg  Gln  Asp  Leu  Glu  Gly  Thr  Pro  Tyr  Leu  Glu  Ser  Gly  Ile
                            1555                     1560                     1565

Ser  Leu  Phe  Ser  Asp  Asp  Pro  Glu  Ser  Asp  Pro  Ser  Glu  Asp  Arg  Ala
                            1570                     1575                     1580

Pro  Glu  Ser  Ala  Arg  Val  Gly  Asn  Ile  Pro  Ser  Ser  Thr  Ser  Ala  Leu
        1585                     1590                     1595                     1600
```

```
Lys Val Pro Gln Leu Lys Val Ala Glu Ser Ala Gln Gly Pro Ala Ala
             1605                1610                1615

Ala His Thr Thr Asp Thr Ala Gly Tyr Asn Ala Met Glu Glu Ser Val
         1620                1625                1630

Ser Arg Glu Lys Pro Glu Leu Thr Ala Ser Thr Glu Arg Val Asn Lys
             1635                1640                1645

Arg Met Ser Met Val Val Ser Gly Leu Thr Pro Glu Glu Phe Met Leu
         1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
             1685                1690                1695

Cys Glu Arg Thr Leu Lys Tyr Phe Leu Gly Ile Ala Gly Gly Lys Trp
             1700                1705                1710

Val Val Ser Tyr Phe Trp Val Thr Gln Ser Ile Lys Glu Arg Lys Met
             1715                1720                1725

Leu Asn Glu His Asp Phe Glu Val Arg Gly Asp Val Val Asn Gly Arg
         1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
             1765                1770                1775

Thr Asp Gln Leu Glu Trp Met Val Gln Leu Cys Gly Ala Ser Val Val
             1780                1785                1790

Lys Glu Leu Ser Ser Phe Thr Leu Gly Thr Gly Val His Pro Ile Val
             1795                1800                1805

Val Val Gln Pro Asp Ala Trp Thr Glu Asp Asn Gly Phe His Ala Ile
         1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
             1845                1850                1855

Gln Ile Pro His Ser His Tyr
             1860
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 2F primer ( x i ) SEQUENCE DESCRIPTION: SEQ ID NO:3:

GAAGTTGTCA TTTTATAAAC CTTT    24

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

(v i) ORIGINAL SOURCE:
     (B) STRAIN: 2R primer (x i) SEQUENCE DESCRIPTION: SEQ ID NO:4:

TGTCTTTTCT TCCCTAGTAT GT                    22

(2) INFORMATION FOR SEQ ID NO:5:

(i) SEQUENCE CHARACTERISTICS:
       (A) LENGTH: 21 base pairs
       (B) TYPE: nucleic acid
       (C) STRANDEDNESS: Not Relevant
       (D) TOPOLOGY: linear (i i) MOLECULE TYPE: DNA (genomic)

(v i) ORIGINAL SOURCE:
       (B) STRAIN: 3F primer (x i) SEQUENCE DESCRIPTION: SEQ ID NO:5:

TCCTGACACA GCAGACATTT A                    21

(2) INFORMATION FOR SEQ ID NO:6:

(i) SEQUENCE CHARACTERISTICS:
       (A) LENGTH: 21 base pairs
       (B) TYPE: nucleic acid
       (C) STRANDEDNESS: Not Relevant
       (D) TOPOLOGY: linear (i i) MOLECULE TYPE: DNA (genomic)

(v i) ORIGINAL SOURCE:
       (B) STRAIN: 3R primer (x i) SEQUENCE DESCRIPTION: SEQ ID NO:6:

TTGGATTTTC GTTCTCACTT A                    21

(2) INFORMATION FOR SEQ ID NO:7:

(i) SEQUENCE CHARACTERISTICS:
       (A) LENGTH: 20 base pairs
       (B) TYPE: nucleic acid
       (C) STRANDEDNESS: Not Relevant
       (D) TOPOLOGY: linear (i i) MOLECULE TYPE: DNA (genomic)

(v i) ORIGINAL SOURCE:
       (B) STRAIN: 5F primer (x i) SEQUENCE DESCRIPTION: SEQ ID NO:7:

CTCTTAAGGG CAGTTGTGAG                      20

(2) INFORMATION FOR SEQ ID NO:8:

(i) SEQUENCE CHARACTERISTICS:
       (A) LENGTH: 20 base pairs
       (B) TYPE: nucleic acid
       (C) STRANDEDNESS: Not Relevant
       (D) TOPOLOGY: linear (i i) MOLECULE TYPE: DNA (genomic)

(v i) ORIGINAL SOURCE:
       (B) STRAIN: 5R-M13* primer (x i) SEQUENCE DESCRIPTION: SEQ ID NO:8:

TTCCTACTGT GGTTGCTTCC                      20

( 2 ) INFORMATION FOR SEQ ID NO:9:

( i ) SEQUENCE CHARACTERISTICS:
            ( A ) LENGTH: 23 base pairs
            ( B ) TYPE: nucleic acid
            ( C ) STRANDEDNESS: Not Relevant
            ( D ) TOPOLOGY: linear ( i i ) MOLECULE TYPE: DNA (genomic)

( v i ) ORIGINAL SOURCE:
           ( B ) STRAIN: 6/7F primer ( x i ) SEQUENCE DESCRIPTION: SEQ ID NO:9:

CTTATTTTAG TGTCCTTAAA AGG                        23

( 2 ) INFORMATION FOR SEQ ID NO:10:

( i ) SEQUENCE CHARACTERISTICS:
            ( A ) LENGTH: 22 base pairs
            ( B ) TYPE: nucleic acid
            ( C ) STRANDEDNESS: Not Relevant
            ( D ) TOPOLOGY: linear ( i i ) MOLECULE TYPE: DNA (genomic)

( v i ) ORIGINAL SOURCE:
           ( B ) STRAIN: 6R ( x i ) SEQUENCE DESCRIPTION: SEQ ID NO:10:

TTTCATGGAC AGCACTTGAG TG                         22

( 2 ) INFORMATION FOR SEQ ID NO:11:

( i ) SEQUENCE CHARACTERISTICS:
            ( A ) LENGTH: 23 base pairs
            ( B ) TYPE: nucleic acid
            ( C ) STRANDEDNESS: Not Relevant
            ( D ) TOPOLOGY: linear ( i i ) MOLECULE TYPE: DNA (genomic)

( v i ) ORIGINAL SOURCE:
           ( B ) STRAIN: 7F primer ( x i ) SEQUENCE DESCRIPTION: SEQ ID NO:11:

CACAACAAAG AGCATACATA GGG                        23

( 2 ) INFORMATION FOR SEQ ID NO:12:

( i ) SEQUENCE CHARACTERISTICS:
           ( A ) LENGTH: 20 base pairs
            ( B ) TYPE: nucleic acid
            ( C ) STRANDEDNESS: Not Relevant
            ( D ) TOPOLOGY: linear ( i i ) MOLECULE TYPE: DNA (genomic)

( v i ) ORIGINAL SOURCE:
           ( B ) STRAIN: 6/7R primer ( x i ) SEQUENCE DESCRIPTION: SEQ ID NO:12:

TCGGGTTCAC TCTGTAGAAG                            20

( 2 ) INFORMATION FOR SEQ ID NO:13:

( i ) SEQUENCE CHARACTERISTICS:
            ( A ) LENGTH: 21 base pairs
            ( B ) TYPE: nucleic acid
            ( C ) STRANDEDNESS: Not Relevant
            ( D ) TOPOLOGY: linear ( i i ) MOLECULE TYPE: DNA (genomic)

( v i ) ORIGINAL SOURCE:
    ( B ) STRAIN: 8F1 primer ( x i ) SEQUENCE DESCRIPTION: SEQ ID NO:13:

```
TTCTCTTCAG GAGGAAAAGC A                                          21
```

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 8R1 primer ( x i ) SEQUENCE DESCRIPTION: SEQ ID NO:14:

```
GCTGCCTACC ACAAATACAA A                                          21
```

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 9F primer ( x i ) SEQUENCE DESCRIPTION: SEQ ID NO:15:

```
CCACAGTAGA TGCTCAGTAA ATA                                        23
```

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 9R primer ( x i ) SEQUENCE DESCRIPTION: SEQ ID NO:16:

```
TAGGAAAATA CCAGCTTCAT AGA                                        23
```

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 10F primer ( x i ) SEQUENCE DESCRIPTION: SEQ ID NO:17:

```
TGGTCAGCTT TCTGTAATCG                                            20
```

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 10R primer ( x i ) SEQUENCE DESCRIPTION: SEQ ID NO:18:

GTATCTACCC ACTCTCTTCT TCAG        24

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11AF primer ( x i ) SEQUENCE DESCRIPTION: SEQ ID NO:19:

CCACCTCCAA GGTGTATCA        19

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11AR primer ( x i ) SEQUENCE DESCRIPTION: SEQ ID NO:20:

TGTTATGTTG GCTCCTTGCT        20

( 2 ) INFORMATION FOR SEQ ID NO:21:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11BF1 primer ( x i ) SEQUENCE DESCRIPTION: SEQ ID NO:21:

CACTAAAGAC AGAATGAATC TA        22

( 2 ) INFORMATION FOR SEQ ID NO:22:

( i ) SEQUENCE CHARACTERISTICS:
        ( A ) LENGTH: 22 base pairs
        ( B ) TYPE: nucleic acid
        ( C ) STRANDEDNESS: Not Relevant ( D ) TOPOLOGY: linear ( i i ) MOLECULE TYPE: DNA (genomic)

( v i ) ORIGINAL SOURCE:
      ( B ) STRAIN: 11BR1 primer ( x i ) SEQUENCE DESCRIPTION: SEQ ID NO:22:

GAAGAACCAG AATATTCATC TA 22

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11CF1 primer ( x i ) SEQUENCE DESCRIPTION: SEQ ID NO:23:

TGATGGGGAG TCTGAATCAA 20

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11CR1 primer ( x i ) SEQUENCE DESCRIPTION: SEQ ID NO:24:

TCTGCTTTCT TGATAAAATC CT 22

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11DF1 primer ( x i ) SEQUENCE DESCRIPTION: SEQ ID NO:25:

AGCGTCCCCT CACAAATAAA 20

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11DR1 primer ( x i ) SEQUENCE DESCRIPTION: SEQ ID NO:26:

```
TCAAGCGCAT GAATATGCCT                                                    20
```

( 2 ) INFORMATION FOR SEQ ID NO:27:

( i ) SEQUENCE CHARACTERISTICS:
    ( A ) LENGTH: 22 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 11EF primer ( x i ) SEQUENCE DESCRIPTION: SEQ ID NO:27:

```
GTATAAGCAA TATGGAACTC GA                                                 22
```

( 2 ) INFORMATION FOR SEQ ID NO:28:

( i ) SEQUENCE CHARACTERISTICS:
    ( A ) LENGTH: 23 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 11ER primer ( x i ) SEQUENCE DESCRIPTION: SEQ ID NO:28:

```
TTAAGTTCACT GGTATTTGAA CA                                                23
```

( 2 ) INFORMATION FOR SEQ ID NO:29:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 11FF primer ( x i ) SEQUENCE DESCRIPTION: SEQ ID NO:29:

```
GACAGCGATA CTTTCCCAGA                                                    20
```

( 2 ) INFORMATION FOR SEQ ID NO:30:

( i ) SEQUENCE CHARACTERISTICS:
    ( A ) LENGTH: 21 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 11FR primer ( x i ) SEQUENCE DESCRIPTION: SEQ ID NO:30:

```
TGGAACAACC ATGAATTAGT C                                                  21
```

( 2 ) INFORMATION FOR SEQ ID NO:31:

( i ) SEQUENCE CHARACTERISTICS:
    ( A ) LENGTH: 20 base pairs ( B ) TYPE: nucleic acid
( C ) STRANDEDNESS: Not Relevant
( D ) TOPOLOGY: linear ( i i ) MOLECULE TYPE: DNA (genomic)

( v i ) ORIGINAL SOURCE:
( B ) STRAIN: 11GF primer ( x i ) SEQUENCE DESCRIPTION: SEQ ID NO:31:

GGAAGTTAGC ACTCTAGGGA     20

( 2 ) INFORMATION FOR SEQ ID NO:32:

( i ) SEQUENCE CHARACTERISTICS:
( A ) LENGTH: 22 base pairs
( B ) TYPE: nucleic acid
( C ) STRANDEDNESS: Not Relevant
( D ) TOPOLOGY: linear ( i i ) MOLECULE TYPE: DNA (genomic)

( v i ) ORIGINAL SOURCE:
( B ) STRAIN: 11GR primer ( x i ) SEQUENCE DESCRIPTION: SEQ ID NO:32:

GCAGTGATAT TAACTGTCTG TA     22

( 2 ) INFORMATION FOR SEQ ID NO:33:

( i ) SEQUENCE CHARACTERISTICS:
( A ) LENGTH: 22 base pairs
( B ) TYPE: nucleic acid
( C ) STRANDEDNESS: Not Relevant
( D ) TOPOLOGY: linear ( i i ) MOLECULE TYPE: DNA (genomic)

( v i ) ORIGINAL SOURCE:
( B ) STRAIN: 11HF primer ( x i ) SEQUENCE DESCRIPTION: SEQ ID NO:33:

TGGGTCCTTA AAGAAACAAA GT     22

( 2 ) INFORMATION FOR SEQ ID NO:34:

( i ) SEQUENCE CHARACTERISTICS:
( A ) LENGTH: 21 base pairs
( B ) TYPE: nucleic acid
( C ) STRANDEDNESS: Not Relevant
( D ) TOPOLOGY: linear ( i i ) MOLECULE TYPE: DNA (genomic)

( v i ) ORIGINAL SOURCE:
( B ) STRAIN: 11HR primer ( x i ) SEQUENCE DESCRIPTION: SEQ ID NO:34:

TCAGGTGACA TTGAATCTTC C     21

( 2 ) INFORMATION FOR SEQ ID NO:35:

( i ) SEQUENCE CHARACTERISTICS:
( A ) LENGTH: 21 base pairs
( B ) TYPE: nucleic acid
( C ) STRANDEDNESS: Not Relevant
( D ) TOPOLOGY: linear ( i i ) MOLECULE TYPE: DNA (genomic)

( v i ) ORIGINAL SOURCE:
( B ) STRAIN: 11IF primer ( x i ) SEQUENCE DESCRIPTION: SEQ ID NO:35:

CCACTTTTTC CCATCAAGTC A                                     21

( 2 ) INFORMATION FOR SEQ ID NO:36:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11IR primer ( x i ) SEQUENCE DESCRIPTION: SEQ ID NO:36:

TCAGGATGCT TACAATTACT TC                                    22

( 2 ) INFORMATION FOR SEQ ID NO:37:

( i ) SEQUENCE CHARACTERISTICS:
        ( A ) LENGTH: 23 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11JF primer ( x i ) SEQUENCE DESCRIPTION: SEQ ID NO:37:

CAAAATTGAA TGCTATGCTT AGA                                   23

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11JR primer ( x i ) SEQUENCE DESCRIPTION: SEQ ID NO:38:

TCGGTACCCC TGAGCCAAAT                                       20

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 11KF primer ( x i ) SEQUENCE DESCRIPTION: SEQ ID NO:39:

GCAAAAGCGT CCAGAAAGGA                                       20

( 2 ) INFORMATION FOR SEQ ID NO:40:

( i ) SEQUENCE CHARACTERISTICS:
    ( A ) LENGTH: 22 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 11KR-1 primer ( x i ) SEQUENCE DESCRIPTION: SEQ ID NO:40:

TATTTGCAGT CAAGTCTTCC AA                    22

( 2 ) INFORMATION FOR SEQ ID NO:41:

( i ) SEQUENCE CHARACTERISTICS:
    ( A ) LENGTH: 21 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 11LF-1 primer ( x i ) SEQUENCE DESCRIPTION: SEQ ID NO:41:

GTAATATTGG CAAAGGCATC T                     21

( 2 ) INFORMATION FOR SEQ ID NO:42:

( i ) SEQUENCE CHARACTERISTICS:
    ( A ) LENGTH: 22 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 11LR primer ( x i ) SEQUENCE DESCRIPTION: SEQ ID NO:42:

TAAAATGTGC TCCCCAAAAG CA                    22

( 2 ) INFORMATION FOR SEQ ID NO:43:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 12F primer ( x i ) SEQUENCE DESCRIPTION: SEQ ID NO:43:

GTCCTGCCAA TGAGAAGAAA                       20

( 2 ) INFORMATION FOR SEQ ID NO:44:

( i ) SEQUENCE CHARACTERISTICS:
    ( A ) LENGTH: 21 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
   ( B ) STRAIN: 12R primer ( x i ) SEQUENCE DESCRIPTION: SEQ ID NO:44:

TGTCAGCAAA CCTAAGAATG T　　　　　　　　　　　　　　　　　　　　　　　　21

( 2 ) INFORMATION FOR SEQ ID NO:45:

( i ) SEQUENCE CHARACTERISTICS:
      ( A ) LENGTH: 21 base pairs
      ( B ) TYPE: nucleic acid
      ( C ) STRANDEDNESS: Not Relevant
      ( D ) TOPOLOGY: linear ( i i ) MOLECULE TYPE: DNA (genomic)

( v i ) ORIGINAL SOURCE:
      ( B ) STRAIN: 13F primer ( x i ) SEQUENCE DESCRIPTION: SEQ ID NO:45:

AATGGAAAGC TTCTCAAAGT A　　　　　　　　　　　　　　　　　　　　　　　　21

( 2 ) INFORMATION FOR SEQ ID NO:46:

( i ) SEQUENCE CHARACTERISTICS:
      ( A ) LENGTH: 21 base pairs
      ( B ) TYPE: nucleic acid
      ( C ) STRANDEDNESS: Not Relevant
      ( D ) TOPOLOGY: linear ( i i ) MOLECULE TYPE: DNA (genomic)

( v i ) ORIGINAL SOURCE:
      ( B ) STRAIN: 13R primer ( x i ) SEQUENCE DESCRIPTION: SEQ ID NO:46:

ATGTTGGAGC TAGGTCCTTA C　　　　　　　　　　　　　　　　　　　　　　　　21

( 2 ) INFORMATION FOR SEQ ID NO:47:

( i ) SEQUENCE CHARACTERISTICS:
      ( A ) LENGTH: 22 base pairs
      ( B ) TYPE: nucleic acid
      ( C ) STRANDEDNESS: Not Relevant
      ( D ) TOPOLOGY: linear ( i i ) MOLECULE TYPE: DNA (genomic)

( v i ) ORIGINAL SOURCE:
      ( B ) STRAIN: 14F primer ( x i ) SEQUENCE DESCRIPTION: SEQ ID NO:47:

CTAACCTGAA TTATCACTAT CA　　　　　　　　　　　　　　　　　　　　　　　22

( 2 ) INFORMATION FOR SEQ ID NO:48:

( i ) SEQUENCE CHARACTERISTICS:
      ( A ) LENGTH: 21 base pairs
      ( B ) TYPE: nucleic acid
      ( C ) STRANDEDNESS: Not Relevant
      ( D ) TOPOLOGY: linear ( i i ) MOLECULE TYPE: DNA (genomic)

( v i ) ORIGINAL SOURCE:
      ( B ) STRAIN: 14R primer ( x i ) SEQUENCE DESCRIPTION: SEQ ID NO:48:

GTGTATAAAT GCCTGTATGC A　　　　　　　　　　　　　　　　　　　　　　　　21

( 2 ) INFORMATION FOR SEQ ID NO:49:

( i ) SEQUENCE CHARACTERISTICS:
    ( A ) LENGTH: 19 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 15F primer ( x i ) SEQUENCE DESCRIPTION: SEQ ID NO:49:

TGGCTGCCCA GGAAGTATG                 19

( 2 ) INFORMATION FOR SEQ ID NO:50:

( i ) SEQUENCE CHARACTERISTICS:
    ( A ) LENGTH: 23 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 15R primer ( x i ) SEQUENCE DESCRIPTION: SEQ ID NO:50:

AACCAGAATA TCTTTATGTA GGA             23

( 2 ) INFORMATION FOR SEQ ID NO:51:

( i ) SEQUENCE CHARACTERISTICS:
    ( A ) LENGTH: 22 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 16F primer ( x i ) SEQUENCE DESCRIPTION: SEQ ID NO:51:

AATTCTTAAC AGAGACCAGA AC              22

( 2 ) INFORMATION FOR SEQ ID NO:52:

( i ) SEQUENCE CHARACTERISTICS:
    ( A ) LENGTH: 22 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 16R primer ( x i ) SEQUENCE DESCRIPTION: SEQ ID NO:52:

AAAACTCTTT CCAGAATGTT GT              22

( 2 ) INFORMATION FOR SEQ ID NO:53:

( i ) SEQUENCE CHARACTERISTICS:
    ( A ) LENGTH: 20 base pairs
    ( B ) TYPE: nucleic acid
    ( C ) STRANDEDNESS: Not Relevant
    ( D ) TOPOLOGY: linear ( i i ) MOLECULE TYPE: DNA (genomic)

( v i ) ORIGINAL SOURCE:
    ( B ) STRAIN: 17F primer ( x i ) SEQUENCE DESCRIPTION: SEQ ID NO:53:

GTGTAGAACG TGCAGGATTG 20

( 2 ) INFORMATION FOR SEQ ID NO:54:

( i ) SEQUENCE CHARACTERISTICS:
        ( A ) LENGTH: 18 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 17R primer ( x i ) SEQUENCE DESCRIPTION: SEQ ID NO:54:

TCGCCTCATG TGGTTTTA 18

( 2 ) INFORMATION FOR SEQ ID NO:55:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 18F primer ( x i ) SEQUENCE DESCRIPTION: SEQ ID NO:55:

GGCTCTTTAG CTTCTTAGGA C 21

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 18R primer ( x i ) SEQUENCE DESCRIPTION: SEQ ID NO:56:

GAGACCATTT TCCCAGCATC 20

( 2 ) INFORMATION FOR SEQ ID NO:57:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 19F primer ( x i ) SEQUENCE DESCRIPTION: SEQ ID NO:57:

CTGTCATTCT TCCTGTGCTC 20

( 2 ) INFORMATION FOR SEQ ID NO:58:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 19R primer ( x i ) SEQUENCE DESCRIPTION: SEQ ID NO:58:

CATTGTTAAG GAAAGTGGTG C      21

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 20F primer ( x i ) SEQUENCE DESCRIPTION: SEQ ID NO:59:

ATATGACGTG TCTGCTCCAC      20

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 20R primer ( x i ) SEQUENCE DESCRIPTION: SEQ ID NO:60:

GGGAATCCAA ATTACACAGC      20

( 2 ) INFORMATION FOR SEQ ID NO:61:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 21F primer ( x i ) SEQUENCE DESCRIPTION: SEQ ID NO:61:

AAGCTCTTCC TTTTGAAAG TC      22

( 2 ) INFORMATION FOR SEQ ID NO:62:

( i ) SEQUENCE CHARACTERISTICS:
        ( A ) LENGTH: 22 base pairs
        ( B ) TYPE: nucleic acid
        ( C ) STRANDEDNESS: Not Relevant (D) TOPOLOGY: linear (ii) MOLECULE TYPE: DNA (genomic)

(vi) ORIGINAL SOURCE:
    (B) STRAIN: 21R primer (xi) SEQUENCE DESCRIPTION: SEQ ID NO:62:

GTAGAGAAAT AGAATAGCCT CT                                              22

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 22F primer (xi) SEQUENCE DESCRIPTION: SEQ ID NO:63:

TCCCATTGAG AGGTCTTGCT                                                 20

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 22R primer (xi) SEQUENCE DESCRIPTION: SEQ ID NO:64:

GAGAAGACTT CTGAGGCTAC                                                 20

(2) INFORMATION FOR SEQ ID NO:65:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 23F-1 primer (xi) SEQUENCE DESCRIPTION: SEQ ID NO:65:

TGAAGTGACA GTTCCAGTAG T                                               21

(2) INFORMATION FOR SEQ ID NO:66:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 23R-1 primer (xi) SEQUENCE DESCRIPTION: SEQ ID NO:66:

CATTTTAGCC ATTCATTCAA CAA                     23

( 2 ) INFORMATION FOR SEQ ID NO:67:

( i ) SEQUENCE CHARACTERISTICS:
        ( A ) LENGTH: 22 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 24F primer ( x i ) SEQUENCE DESCRIPTION: SEQ ID NO:67:

ATGAATTGAC ACTAATCTCT GC                      22

( 2 ) INFORMATION FOR SEQ ID NO:68:

( i ) SEQUENCE CHARACTERISTICS:
        ( A ) LENGTH: 21 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( B ) STRAIN: 24R primer ( x i ) SEQUENCE DESCRIPTION: SEQ ID NO:68:

GTAGCCAGGA CAGTAGAAGG A                       21

( 2 ) INFORMATION FOR SEQ ID NO:69:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:69:

GCAAAAGCGT CCAGAAAGGA                         20

( 2 ) INFORMATION FOR SEQ ID NO:70:

( i ) SEQUENCE CHARACTERISTICS:
        ( A ) LENGTH: 20 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:70:

AGTCTTCCAA TTCACTGCAC                         20

( 2 ) INFORMATION FOR SEQ ID NO:71:

( i ) SEQUENCE CHARACTERISTICS:
        ( A ) LENGTH: 14 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:71:

GAACACAGGA GAAT 14

( 2 ) INFORMATION FOR SEQ ID NO:72:

( i ) SEQUENCE CHARACTERISTICS:
        ( A ) LENGTH: 14 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:72:

TAAGAACACA GGAG 14

( 2 ) INFORMATION FOR SEQ ID NO:73:

( i ) SEQUENCE CHARACTERISTICS:
        ( A ) LENGTH: 16 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:73:

GAACACAGAG GAGAAT 16

( 2 ) INFORMATION FOR SEQ ID NO:74:

( i ) SEQUENCE CHARACTERISTICS:
        ( A ) LENGTH: 16 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:74:

TAAGAACACA GAGGAG 16